(12) United States Patent
Weiser et al.

(10) Patent No.: US 8,921,012 B2
(45) Date of Patent: Dec. 30, 2014

(54) PHOTOPOLYMER FORMULATIONS HAVING THE ADJUSTABLE MECHANICAL MODULUS $G_{UV}$

(75) Inventors: Marc-Stephan Weiser, Leverkusen (DE); Thomas Rölle, Leverkusen (DE); Friedrich-Karl Bruder, Krefeld (DE); Thomas Fäcke, Leverkusen (DE); Dennis Hönel, Zülpich (DE)

(73) Assignee: Bayer MaterialScience AG, Leverkusen (DE)

( * ) Notice: Subject to any disclaimer, the term of this patent is extended or adjusted under 35 U.S.C. 154(b) by 189 days.

(21) Appl. No.: 13/505,501

(22) PCT Filed: Oct. 29, 2010

(86) PCT No.: PCT/EP2010/066456
§ 371 (c)(1),
(2), (4) Date: May 2, 2012

(87) PCT Pub. No.: WO2011/054749
PCT Pub. Date: May 12, 2011

(65) Prior Publication Data
US 2012/0219884 A1 Aug. 30, 2012

(30) Foreign Application Priority Data
Nov. 3, 2009 (EP) .................... 09013771

(51) Int. Cl.
*G01N 11/16* (2006.01)
*G03H 1/02* (2006.01)
*G11B 7/24044* (2013.01)
*G11B 7/245* (2006.01)
*G03F 7/00* (2006.01)
*G03F 7/027* (2006.01)
*G11B 7/0065* (2006.01)

(52) U.S. Cl.
CPC .......... *G01N 11/165* (2013.01); *G11B 7/24044* (2013.01); *G03H 2260/12* (2013.01); *G03H 2001/0264* (2013.01); *G11B 7/245* (2013.01); *G03F 7/001* (2013.01); *G03H 1/02* (2013.01); *G03F 7/027* (2013.01); *G11B 7/0065* (2013.01)
USPC ............. 430/2; 430/1; 430/280.1; 430/281.1; 73/54.26; 359/3

(58) Field of Classification Search
CPC .... C09D 175/08; C08G 18/48; C08G 18/672; C08G 18/79; C08G 18/77; C08G 18/67; C08G 18/78; C08G 18/10; C08L 33/08; C08L 75/04; C08J 5/18; G03H 1/02; G03H 1/04; G11B 7/253; G11B 7/2456; G01N 11/165; G01N 5/04
See application file for complete search history.

(56) References Cited

U.S. PATENT DOCUMENTS 5,470,813 A 11/1995 Le-Khac
5,725,970 A * 3/1998 Martin et al. ............... 430/2

(Continued)

FOREIGN PATENT DOCUMENTS

CA 2362504 A1 8/2000
EP 0223587 A1 5/1987

(Continued)

OTHER PUBLICATIONS

Wypych, Handbook of Plasticizers, Chapter 2, pp. 7-71 (2004).*

(Continued)

*Primary Examiner* — Martin Angebranndt
(74) *Attorney, Agent, or Firm* — Drinker Biddle & Reath LLP

(57) ABSTRACT

The subject matter of the invention is a method for producing illuminated, holographic media comprising a photopolymer formulation having the adjustable mechanical modulus GUV. A further subject matter of the invention is an illuminated, holographic medium that can be obtained by means of the method according to the invention.

17 Claims, 11 Drawing Sheets

(56) References Cited

U.S. PATENT DOCUMENTS

| | | | |
|---|---|---|---|
| 6,627,354 B1* | 9/2003 | Chandross et al. | 430/1 |
| 8,222,314 B2* | 7/2012 | Roelle et al. | 522/174 |
| 8,329,773 B2* | 12/2012 | Facke et al. | 522/97 |
| 8,361,678 B2* | 1/2013 | Weiser et al. | 430/1 |
| 8,530,540 B2* | 9/2013 | Kodama | 522/182 |
| 2002/0142227 A1* | 10/2002 | Dhar et al. | 430/1 |
| 2002/0150712 A1* | 10/2002 | Ohtaki et al. | 428/40.1 |
| 2002/0167735 A1* | 11/2002 | Jethmalani et al. | 359/642 |
| 2003/0044691 A1* | 3/2003 | Setthachayanon et al. | 430/1 |
| 2005/0013959 A1 | 1/2005 | Ohtaki et al. | |
| 2006/0128822 A1* | 6/2006 | Katou et al. | 522/7 |
| 2007/0070477 A1* | 3/2007 | Eto et al. | 359/12 |
| 2007/0172742 A1* | 7/2007 | Yachi et al. | 430/1 |
| 2008/0161444 A1* | 7/2008 | Hayashi et al. | 522/81 |
| 2009/0012202 A1* | 1/2009 | Jacobine et al. | 522/90 |
| 2009/0087753 A1* | 4/2009 | Satou et al. | 430/2 |
| 2010/0036013 A1 | 2/2010 | Roelle et al. | |
| 2010/0086860 A1* | 4/2010 | Roelle et al. | 430/2 |
| 2010/0086861 A1* | 4/2010 | Weiser et al. | 430/2 |
| 2010/0087564 A1* | 4/2010 | Weiser et al. | 522/95 |
| 2010/0112459 A1* | 5/2010 | Weiser et al. | 430/2 |
| 2010/0203241 A1* | 8/2010 | Weiser et al. | 427/162 |
| 2010/0247839 A1* | 9/2010 | Hayashida et al. | 428/64.4 |
| 2011/0065827 A1 | 3/2011 | Facke et al. | |
| 2011/0189591 A1* | 8/2011 | Weiser et al. | 430/2 |
| 2011/0207029 A1* | 8/2011 | Hagen et al. | 430/2 |
| 2011/0236803 A1* | 9/2011 | Weiser et al. | 430/2 |
| 2011/0311905 A1* | 12/2011 | Honel et al. | 430/2 |
| 2011/0311906 A1* | 12/2011 | Rolle et al. | 430/2 |
| 2012/0214089 A1* | 8/2012 | Honel et al. | 430/2 |
| 2012/0214090 A1* | 8/2012 | Weiser et al. | 430/2 |
| 2012/0214895 A1* | 8/2012 | Rolle et al. | 522/78 |
| 2012/0219883 A1* | 8/2012 | Bruder et al. | 430/2 |
| 2012/0219885 A1* | 8/2012 | Facke et al. | 430/2 |
| 2012/0231376 A1* | 9/2012 | Rolle et al. | 430/2 |
| 2012/0231377 A1* | 9/2012 | Weiser et al. | 430/2 |
| 2012/0237856 A1* | 9/2012 | Rolle et al. | 430/2 |
| 2012/0302659 A1* | 11/2012 | Rolle et al. | 522/173 |
| 2012/0321997 A1* | 12/2012 | Rolle et al. | 430/2 |
| 2012/0321998 A1* | 12/2012 | Rolle et al. | 430/2 |
| 2013/0224634 A1* | 8/2013 | Berneth et al. | 430/2 |
| 2013/0252140 A1* | 9/2013 | Facke et al. | 430/2 |

FOREIGN PATENT DOCUMENTS

| | | | |
|---|---|---|---|
| EP | 0700949 A2 | | 3/1996 |
| EP | 0743093 A1 | | 11/1996 |
| EP | 0761708 A2 | | 3/1997 |
| EP | 2110718 | * | 10/2009 |
| EP | 2154129 A1 | | 2/2010 |
| EP | 09009651.2 | | 2/2010 |
| EP | 2219075 A1 | | 8/2010 |
| EP | 09002180.9 | | 8/2010 |
| WO | WO-97/40086 A1 | | 10/1997 |
| WO | WO-98/16310 A1 | | 4/1998 |
| WO | WO-00/47649 A1 | | 8/2000 |
| WO | WO-2008/125229 A1 | | 10/2008 |

OTHER PUBLICATIONS

Anton Parr, Instruction Manual Physica MCR series, Physica MCR 51/101/301/501, Physica Smartpave 42 pages (2006).*

International Search Report for PCT/EP2010/066456 mailed Dec. 23, 2010.

* cited by examiner

PHOTOPOLYMER FORMULATIONS HAVING THE ADJUSTABLE MECHANICAL MODULUS $G_{UV}$

CROSS-REFERENCE TO RELATED APPLICATIONS

This application is a national stage application (under 35 U.S.C. §371) of PCT/EP2010/066456, filed Oct. 29, 2010, which claims benefit of European application 09013771.2, filed Nov. 3, 2009, both of which are incorporated herein by reference in their entirety for all their useful purposes.

BACKGROUND

The invention relates to a process for the production of exposed, holographic media containing a photopolymer formulation. The invention furthermore relates to an exposed holographic medium which is obtainable by the process according to the invention.

WO 2008/125229 A1 describes photopolymer formulations which can be used for the production of holographic media. The photopolymer formulations disclosed comprise polyurethane-based matrix polymers, acrylate-based writing monomers and photoinitiators. The holographic media obtainable with the aid of the photopolymer formulations are distinguished by high brightness, which is described physically by their high refractive index contrast ($\Delta n$).

In the known process, it is not possible to vary the mechanical properties of the exposed holographic media obtained on keeping $\Delta n$ substantially constant. Thus on modification of these properties by changing the chemical composition, the $\Delta n$ value also changes here. A variation of the mechanical properties without significant change in the refractive index contrast is, however, desirable in many cases since, depending on the field of use, holographic media have to meet very different requirements with regard to the mechanical properties. Thus, for example, media having a mechanical modulus of less than 0.7 MPa can be laminated with a substrate without additional adhesive. On the other hand, it may be desirable to obtain media which are insensitive to damage due to external influences. This can be ensured when the media have a high modulus in the region of 15 MPa or more.

Furthermore, particularly when holograms are used as a security feature, it is of decisive importance to be able to adjust the mechanical properties according to wishes without the $\Delta n$ value significantly changing at the same time. Thus, it may be desirable in particular that an exposed holographic medium cannot be removed without destruction from a marked product, such as an identity document. Media with a flexible rubber-like consistency which have a correspondingly low modulus in the region of less than 0.7 MPa are suitable for this purpose. Conversely, however, it may also be necessary in particular to permit destruction-free transfer. In this case, the medium should have relatively high rigidity, which corresponds to a modulus in the region of 15 MPa or more. These different aspects cannot be realised by the process known in the prior art.

BRIEF DESCRIPTION OF EMBODIMENTS

It was therefore an object of the present invention to provide a process for the production of exposed holographic media, with the aid of which media having a modulus $G_{UV}$ variable in the range between 0.1 and 160 MPa and a $\Delta n \geq 0.008$ can be obtained.

This object is achieved by a process in which
i) a photopolymer formulation comprising
   A) matrix polymers as an amorphous network
   B) a combination of a monofunctional writing monomer and a polyfunctional writing monomer
   C) a photoinitiator system
   D) optionally a non-photopolymerisable component
   E) optionally catalysts, free radical stabilisers, solvents, additives and other auxiliaries and/or additives is provided,
ii) the photopolymer formulation is brought into the form of media
iii) the media are subjected to a holographic exposure experiment in order to record the hologram and
iv) the medium as a whole is exposed to UV radiation in order to fix the hologram, the writing monomers being acrylate- and/or methacrylate-functionalised compounds, the total content of writing monomers in the photopolymer formulation being ≥30% by weight and ≤45% by weight, the unexposed photopolymer formulation having a modulus $G_0$ of <0.7 MPa and the modulus $G_{UV}$ of the exposed photopolymer formulation being adjusted in the intended range between 0.1 and 160 MPa via the ratio of the relative proportion of the monofunctional writing monomer to the relative proportion of the polyfunctional writing monomer, based on the total writing monomer content, in such a way that a high modulus is realised by a high relative proportion of the polyfunctional writing monomer and a low modulus by a high relative proportion of the monofunctional writing monomer, based on the total writing monomer content.

With the aid of the process according to the invention, it is possible to obtain holographic media which, after exposure to UV radiation, have a mechanical modulus $G_{UV}$ in the range between 0.1 and 160 MPa. It is therefore possible, depending on the desired profile of use, to produce media which have defined moduli in said range and scarcely differ in their refractive index contrast $\Delta n$. For the producer of the photopolymer formulations, this has the advantage that, with a limited number of suitable components, it is possible to prepare photopolymer formulations which meet different requirements with regard to their application and their use, in which the mechanical modulus is decisive, without the end user having to accept compromises in the brightness of the holograms.

In particular, the exposed, holographic media may have a modulus $G_{UV}$ in the range between 0.3 and 40, preferably between 0.7 and 15, MPa.

According to a preferred embodiment of the invention, it is intended that the writing monomers and the matrix polymers are chosen so that the refractive index of each of the two writing monomers is either at least 0.05 unit greater than the refractive index of the matrix polymers or the refractive index of each of the two writing monomers is at least 0.05 unit less than the refractive index of the matrix polymers.

BRIEF DESCRIPTION OF THE DRAWINGS

The foregoing brief description, as well as the following detailed description, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF EMBODIMENTS

Figure 1:
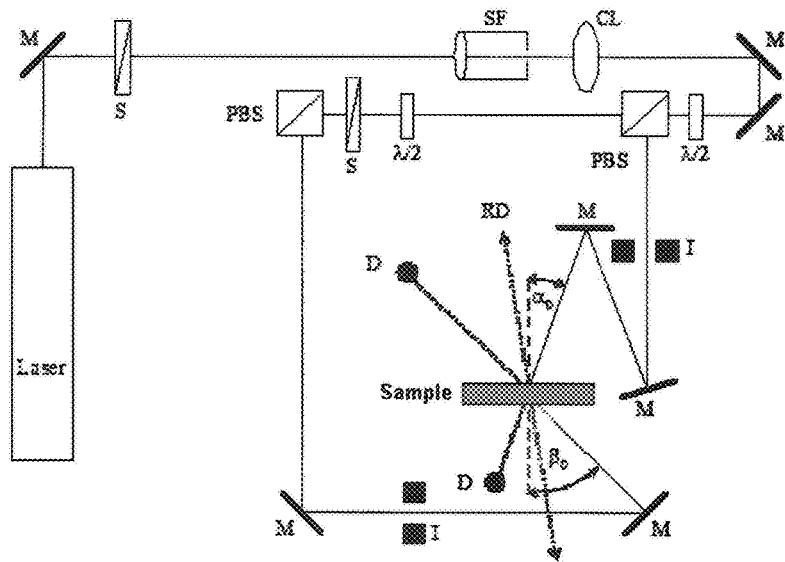
FIG. 1 illustrates a holographic experimental setup to measure the diffraction efficiency (DE) of the media.

The matrix polymers can preferably be polyurethanes. The polyurethanes can be prepared in particular by reacting a component carrying NCO groups and an NCO-reactive components, at least one of the two components having an equivalent weight of more than 200 g/mol, preferably of more than 350 g/mol, and furthermore preferably no cyclic structures occurring in the polymer backbone. Polyurethanes which have a glass transition temperature $T_G < -45°$ C. in the reacted state are particularly preferred.

The matrix polymers A) can preferably be polyurethanes which are obtainable in particular by reacting an isocyanate component a) with an isocyanate-reactive component b).

The isocyanate component a) preferably comprises polyisocyanates. Polyisocyanates which may be used are all compounds known per se to the person skilled in the art or mixtures thereof which have on average two or more NCO functions per molecule. These may have an aromatic, araliphatic, aliphatic or cycloaliphatic basis. In minor amounts, it is also possible concomitantly to use monoisocyanates and/or polyisocyanates containing unsaturated groups.

For example, butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate and/or triphenylmethane 4,4',4"-triisocyanate are suitable.

The use of derivatives of monomeric di- or triisocyanates having urethane, urea, carbodiimide, acylurea, isocyanurate, allophanate, biuret, oxadiazinetrione, uretdione and/or iminooxadiazinedione structures is also possible.

The use of polyisocyanates based on aliphatic and/or cycloaliphatic di- or triisocyanates is preferred.

Particularly preferably, the polyisocyanates of component a) are dimerised or oligomerised aliphatic and/or cycloaliphatic di- or triisocyanates.

Isocyanurates, uretdiones and/or iminooxadiazinediones based on HDI and 1,8-diisocyanato-4-(isocyanatomethyl)octane or mixtures thereof are very particularly preferred.

NCO-functional prepolymers having urethane, allophanate, biuret and/or amide groups can also be used as component a). Prepolymers of component a) are obtained in the manner well known per se to the person skilled in the art by reacting monomeric, oligomeric or polyisocyanates a1) with isocyanate-reactive compounds a2) in suitable stoichiometry with optional use of catalysts and solvents.

Suitable polyisocyanates a1) are all aliphatic, cycloaliphatic, aromatic or araliphatic di- and triisocyanates known per se to the person skilled in the art, it being unimportant whether they were obtained by means of phosgenation or by phosgene-free processes. In addition, the higher molecular weight secondary products of monomeric di- and/or triisocyanates having a urethane, urea, carbodiimide, acylurea, isocyanurate, allophanate, biuret, oxadiazinetrione, uretdione or iminooxadiazinedione structure, which are well known per se to the person skilled in the art, can also be used, in each case individually or as any desired mixtures with one another.

Examples of suitable monomeric di- or triisocyanates which can be used as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds a2) for the synthesis of the prepolymers. These are analogous to the OH-functional compounds as described below for component b).

Preferred OH-functional compounds in a2) are polyester- and/or polyetherpolyols having number average molar masses of 200 to 6200 g/mol. Difunctional polyetherpolyols based on ethylene glycol and propylene glycol, the proportion of propylene glycol accounting for at least 40% by weight, and polymers of tetrahydrofuran having number average molar masses of 200 to 4100 g/mol and aliphatic polyesterpolyols having number average molar masses of 200 to 3100 g/mol are particularly preferred.

Difunctional polyetherpolyols based on ethylene glycol and propylene glycol, the proportion of propylene glycol accounting for at least 80% by weight (in particular pure polypropylene glycols), and polymers of tetrahydrofuran having number average molar masses of 200 to 2100 g/mol are very particularly preferred. Adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms) are also very particularly preferred. These adducts preferably have number average molar masses of 200 to 2000 g/mol, particularly preferably of 500 to 1400 g/mol.

Allophanates can also be used as a mixture with other prepolymers or oligomers of component a1). In these cases, the use of OH-functional compounds having functionalities of 1 to 3.1 is advantageous. With the use of monofunctional alcohols, those having 3 to 20 carbon atoms are preferred.

It is also possible to use amines for the prepolymer preparation. For example, ethylenediamine, diethylenetriamine, triethylenetetramine, propylenediamine, diaminocyclohexane, diaminobenzene, diaminobisphenyl, difunctional polyamines, such as, for example, the Jeffamines®, amine-terminated polymers having number average molar masses of up to 10 000 g/mol or any desired mixtures thereof with one another are suitable.

For the preparation of prepolymers containing biuret groups, isocyanate is reacted in excess with amine, a biuret group forming. Suitable amines in this case for the reaction with the di-, tri- and polyisocyanates mentioned are all oligomeric or polymeric, primary or secondary, difunctional amines of the abovementioned type. Aliphatic biurets based on aliphatic amines and aliphatic isocyanates are preferred. Low molecular weight biurets having number average molar masses of less than 2000 g/mol, based on aliphatic diamines or difunctional polyamines and aliphatic diisocyanates, in particular HDI and TMDI, are particularly preferred.

Preferred prepolymers are urethanes, allophanates or biurets obtained from aliphatic isocyanate-functional compounds and oligomeric or polymeric isocyanate-reactive compounds having number average molar masses of 200 to 10 000 g/mol; urethanes, allophanates or biurets obtained from aliphatic isocyanate-functional compounds and polyols having number average molar masses of 200 to 6200 g/mol or (poly)amines having number average molar masses of less than 3000 g/mol are particularly preferred and allophanates obtained from HDI or TMDI and difunctional polyetherpolyols (in particular polypropylene glycols) having number average molar masses of 200 to 2100 g/mol, urethanes obtained from HDI or TMDI based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms) having number average molar masses of 500 to 3000 g/mol, particularly preferably of 1000 to 2000 g/mol (in particular as a mixture with other oligomers of difunctional aliphatic isocyanates) or urethanes obtained from HDI or TMDI based on trifunctional polyetherpolyols (in particular polypropylene glycol) having number average molar masses between 2000 and 6200 g/mol and biurets obtained from HDI or TMDI with difunctional amines or polyamines having number average molar masses of 200 to 1400 g/mol (in particular as a mixture with other oligomers of difunctional aliphatic isocyanates) are very particularly preferred.

Preferably, the prepolymers described above have residual contents of free monomeric isocyanate of less than 2% by weight, particularly preferably less than 1.0% by weight, very particularly preferably less than 0.5% by weight.

Of course, the isocyanate component may contain further isocyanate components proportionately in addition to the prepolymers described. Aromatic, araliphatic, aliphatic and cycloaliphatic di-, tri- or polyisocyanates are suitable for this purpose used. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate, triphenylmethane 4,4',4"-triisocyanate or derivatives thereof having a urethane, urea, carbodiimide, acylurea, isocyanurate, allophanate, biuret, oxadiazinetrione, uretdione or iminooxadiazinedione structure and mixtures thereof. Polyisocyanates based on oligomerised and/or derivatised diisocyanates which were freed from excess diisocyanate by suitable processes are preferred, in particular those of hexamethylene diisocyanate. The oligomeric isocyanurates, uretdiones and iminooxadiazinediones of HDI and mixtures thereof are particularly preferred.

It is optionally also possible for the isocyanate component a) proportionately to contain isocyanates which are partly reacted with isocyanate-reactive ethylenically unsaturated compounds. α,β-unsaturated carboxylic acid derivatives, such as acrylates, methacrylates, maleates, fumarates, maleimides, acrylamides, and vinyl ethers, propenyl ethers, allyl ethers and compounds containing dicyclopentadienyl units, which have at least one group reactive toward isocyanates, are preferably used here as isocyanate-reactive ethylenically unsaturated compounds; these are particularly preferably acrylates and methacrylates having at least one isocyanate-reactive group. Suitable hydroxy-functional acrylates or methacrylates are, for example, compounds such as 2-hydroxyethyl(meth)acrylate, polyethylene oxide mono(meth)acrylates, polypropylene oxide mono-(meth)acrylates, polyalkylene oxide mono(meth)acrylates, poly(ε-caprolactone) mono(meth)acrylates, such as, for example, Tone® M100 (Dow, USA), 2-hydroxypropyl(meth)acrylate, 4-hydroxybutyl(meth)acrylate, 3-hydroxy-2,2-dimethylpropyl(meth)acrylate, the hydroxy-functional mono-, di- or tetra(meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which are partly reacted with isocyanate-reactive ethylenically unsaturated compounds is 0 to 99%, preferably 0 to 50%, particularly preferably 0 to 25% and very particularly preferably 0 to 15%, based on the isocyanate component a).

It is optionally also possible for the abovementioned isocyanate component a) completely or proportionately to contain isocyanates which are reacted completely or partly with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or any desired mixtures of these blocking agents.

All polyfunctional, isocyanate-reactive compounds which have on average at least 1.5 isocyanate-reactive groups per molecule can be used per se as component b).

In the context of the present invention, isocyanate-reactive groups are preferably hydroxyl, amino or thio groups; hydroxy compounds are particularly preferred.

Suitable polyfunctional, isocyanate-reactive compounds are, for example, polyester-, polyether-, polycarbonate-, poly (meth)acrylate- and/or polyurethanepolyols.

In addition, aliphatic, araliphatic or cycloaliphatic di-, tri- or polyfunctional alcohols having a low molecular weight, i.e. having molecular weights of less than 500 g/mol, and short chains, i.e. containing 2 to 20 carbon atoms, are also suitable as polyfunctional, isocyanate-reactive compounds as constituents of component b).

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butylpropanediol, trimethylpentanediol, positional isomers of diethyloctanediol, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxypropionic acid (2,2-dimethyl-3-hydroxypropyl ester). Examples of suitable triols are trimethylolethane, trimethylolpropane or glycerol. Suitable alcohols having a higher functionality are ditrimethylolpropane, pentaerythritol, dipentaerythritol or sorbitol.

Suitable polyesterpolyols are, for example, linear polyesterdiols or branched polyesterpolyols, as are obtained in a known manner from aliphatic, cycloaliphatic or aromatic di- or polycarboxylic acids or their anhydrides with polyhydric alcohols having an OH functionality of ≥2.

Examples of such di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides such as o-phthalic, trimellitic or succinic anhydride, or any desired mixtures thereof with one another.

Examples of such suitable alcohols are ethanediol, di-, tri- and tetraethylene glycol, 1,2-propanediol, di-, tri- and tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any desired mixtures thereof with one another.

Preferred polyesterpolyols are based on aliphatic alcohols and mixtures of aliphatic and aromatic acids and have number average molar masses between 500 and 10 000 g/mol and functionalities between 1.8 and 6.1.

Particularly preferred polyesterpolyols are based on aliphatic diols, such as butane-1,4-diol, hexane-1,6-diol, neopentylglycol, ethanediol, propylene glycol, 1,3-butylene glycol, di-, tri- and polyethylene glycol, di-, tri- and/or tetrapropylene glycol or mixtures of abovementioned diols with aliphatic alcohols having a higher functionality, such as trimethylolpropane and/or pentaerythritol, the proportion of the alcohols having a higher functionality preferably accounting for less than 50 percent by weight (particularly preferably less than 30 percent by weight), based on the total amount of the alcohol used, in combination with aliphatic di- or polycarboxylic acids or anhydrides, such as adipic acid and/or succinic acid or mixtures of abovementioned aliphatic polycarboxylic acids or anhydrides with aromatic polycarboxylic acids or anhydrides, such as terephthalic acid and/or isophthalic acid, the proportion of the aromatic polycarboxylic acids or anhydrides preferably accounting for less than 50 percent by weight (particularly preferably less than 30 percent by weight), based on the total amount of the polycarboxylic acids or anhydrides used. Particularly preferred polyesterpolyols have number average molar masses between 1000 and 6000 g/mol and functionalities between 1.9 and 3.3.

The polyesterpolyols may also be based on natural raw materials, such as castor oil. It is also possible for the polyesterpolyols to be based on homo- or copolymers of lactones, as can preferably be obtained by an addition reaction of lactones or lactone mixtures in a ring-opening lactone polymerisation, such as butyrolactone, ε-caprolactone and/or methyl-ε-caprolactone, with hydroxy-functional compounds, such as polyhydric alcohols having an OH functionality of ≥2 or polyols having a functionality of greater than 1.8, for example of the abovementioned type.

Preferred polyols, which are used here as starters, are polyetherpolyols having a functionality of 1.8 to 3.1 and number average molar masses of 200 to 4000 g/mol; poly(tetrahydrofurans) having a functionality of 1.9 to 2.2 and number average molar masses of 500 to 2000 g/mol (in particular 600 to 1400 g/mol) are particularly preferred. As adducts are butyrolactone, ε-caprolactone and/or methyl-ε-caprolactone, ε-caprolactone is particularly preferred.

Such polyesterpolyols preferably have number average molar masses of 400 to 6000 g/mol, particularly preferably of 800 to 3000 g/mol. Their OH functionality is preferably 1.8 to 3.5, particularly preferably 1.9 to 2.2.

Suitable polycarbonatepolyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned in the context of the polyester segments and having an OH functionality of ≥2, preferably 1,4-butanediol, 1,6-hexanediol and/or 3-methylpentanediol, or polyesterpolyols can also be converted into polycarbonatepolyols.

Such polycarbonatepolyols preferably have number average molar masses of 400 to 4000 g/mol, particularly preferably of 500 to 2000 g/mol. The OH functionality of these polyols is preferably 1.8 to 3.2, particularly preferably 1.9 to 3.0.

Suitable polyetherpolyols are polyadducts of cyclic ethers with OH— or NH-functional starter molecules, which polyadducts optionally have a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned in connection with the polyesterpolyols and having an OH functionality of ≥2 and primary and secondary amines and amino alcohols.

Preferred polyetherpolyols are those of the abovementioned type exclusively based on propylene oxide or random or block copolymers based on propylene oxide with further 1-alkylene oxides, the proportion of 1-alkylene oxide being not higher than 80% by weight. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched C3- and C4-isomers.

Such polyetherpolyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1 and very particularly preferably 1.9 to 2.2.

Special polyetherpolyols which are used are preferably those which consist of an isocyanate-reactive component comprising hydroxy-functional multi-block copolymers of the Y(Xi-H)n type, where i=1 to 10 and n=2 to 8, and having number average molecular weights greater than 1500 g/mol, the Xi segments each being composed of oxyalkylene units of the formula (I)

—CH2-CH(R)—O—    Formula (I)

in which R is a hydrogen, alkyl or aryl radical which also may be substituted or may be interrupted by heteroatoms (such as ether oxygens), Y is the underlying starter and the proportion of the Xi segments, based on the total amount of the Xi and Y segments, accounts for at least 50% by weight.

The outer $X_i$ blocks account for at least 50% by weight, preferably 66% by weight, of the total molar mass of $Y(X_i$—$H)_n$ and consist of monomer units which obey the formula (I). Preferably n in $Y(X_i$—$H)_n$ is a number from 2 to 6, particularly preferably 2 or 3 and very particularly preferably 2. Preferably, i in $Y(X_i$—$H)_n$ is a number from 1 to 6, particularly preferably 1 to 3 and very particularly preferably 1.

In formula (I), R is preferably a hydrogen, a methyl, butyl, hexyl or octyl group or an alkyl radical containing ether groups. Preferred alkyl radicals containing ether groups are those based on oxyalkylene units.

The multi-block copolymers $Y(X_i$—$H)_n$ preferably have number average molecular weights of more than 1200 g/mol, particularly preferably more than 1950 g/mol, but preferably not more than 12 000 g/mol, particularly preferably not more than 8000 g/mol.

The $X_i$ blocks may be homopolymers comprising exclusively identical oxyalkylene repeating units. They may also be composed randomly of different oxyalkylene units or in turn blockwise of different oxyalkylene units.

Preferred, the $X_i$ segments are based exclusively on propylene oxide or random or blockwise mixtures of propylene oxide with further 1-alkylene oxides, the proportion of further 1-alkylene oxides being not higher than 80% by weight.

Particularly preferred $X_i$ segments are propylene oxide homopolymers and random or block copolymers which oxyethylene and/or oxypropylene units, the proportion of the oxypropylene units, based on the total amount of all oxyethylene and oxypropylene units, accounting for at least 20% by weight, preferably at least 40% by weight.

The $X_i$ blocks are added to an n-fold hydroxy- or aminofunctional starter block $Y(H)_n$, as described further below, by ring-opening polymerisation of the alkylene oxides described above.

The inner block Y, which is present in an amount of less than 50% by weight, preferably less than 34% by weight, in $Y(X_i$—$H)_n$, consists of dihydroxy-functional and/or higher hydroxy-functional polymer structures based on cyclic ethers or is composed of dihydroxy-functional and/or higher hydroxy-functional polycarbonate, polyester, poly(meth)acrylate, epoxy resin and/or polyurethane structural units or corresponding hybrids.

Suitable polyesterpolyols are linear polyesterdiols or branched polyesterpolyols, as can be prepared in a known manner from aliphatic, cycloaliphatic or aromatic di- or polycarboxylic acids or their anhydrides, such as, for example, succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid, and acid anhydrides, such as o-phthalic, trimellitic or succinic anhydride, or any desired mixtures thereof with polyhydric alcohols, such as, for example, ethanediol, di-, tri- or tetraethylene glycol, 1,2-propanediol, di-, tri- or tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol or mixtures thereof, optionally with concomitant use of polyols having higher functionality, such as trimethylolpropane or glycerol. Of course, cycloaliphatic and/or aromatic di- and polyhydroxy compounds are also suitable as polyhydric alcohols for the preparation of the polyesterpolyols. Instead of the free polycarboxylic acid, it is also possible to use the corresponding polycarboxylic anhydrides or corresponding polycarboxylic esters of lower alcohols or mixtures thereof for the preparation of the polyesters.

The polyesterpolyols may also be based on natural raw materials, such as castor oil. It is also possible for the polyesterpolyols to be based on homo- or copolymers of lactones, as can preferably be obtained by an addition reaction of lactones or lactone mixtures, such as butyrolactone, ε-caprolactone and/or methyl-ε-caprolactone, with hydroxy-functional compounds, such as polyhydric alcohols having an OH functionality of preferably 2, for example of the abovementioned type.

Such polyesterpolyols preferably have number average molar masses of 200 to 2000 g/mol, particularly preferably of 400 to 1400 g/mol.

Suitable polycarbonatepolyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned per se in connection with the polyesterpolyols and having an OH functionality of 2, preferably 1,4-butanediol, 1,6-hexanediol and/or 3-methylpentanediol. Polyesterpolyols can also be converted into polycarbonatepolyols. Dimethyl or diethyl carbonate is particularly preferably used in the conversion of said alcohols into polycarbonatepolyols.

Such polycarbonatepolyols preferably have number average molar masses of 400 to 2000 g/mol, particularly preferably of 500 to 1400 g/mol and very particularly preferably of 650 to 1000 g/mol.

Suitable polyetherpolyols are polyadducts of cyclic ethers with OH— or NH-functional starter molecules, which polyadducts optionally have a block structure. For example, the polyadducts of styrene oxides, of ethylene oxide, propylene oxide, tetrahydrofuran, butylene oxide, epichlorohydrin and their mixed adducts and graft products and the polyetherpolyols obtained by condensation of polyhydric alcohols or mixtures thereof and the polyetherpolyols obtained by alkoxylation of polyhydric alcohols, amines and amino alcohols may be mentioned as polyetherpolyols.

Suitable polymers of cyclic ethers are in particular polymers of tetrahydrofuran.

Starters which may be used are the polyhydric alcohols mentioned per se in connection with the polyesterpolyols and primary or secondary amines and amino alcohols having an OH or NH functionality of 2 to 8, preferably 2 to 6, particularly preferably 2 to 3, very particularly preferably 2.

Such polyetherpolyols preferably have number average molar masses of 200 to 2000 g/mol, particularly preferably of 400 to 1400 g/mol and very particularly preferably of 650 to 1000 g/mol.

The polymers of tetrahydrofuran are preferably employed as polyetherpolyols used for starters.

Of course, mixtures of the components described above can also be used for the inner block Y.

Preferred components for the inner block Y are polymers of tetrahydrofuran and aliphatic polycarbonatepolyols and polyesterpolyols and polymers of ε-caprolactone having number average molar masses of less than 3100 g/mol.

Particularly preferred components for the inner block Y are difunctional polymers of tetrahydrofuran and difunctional aliphatic polycarbonatepolyols and polyesterpolyols and polymers of ε-caprolactone having number average molar masses of less than 3100 g/mol.

Very particularly preferably, the starter segment Y is based on difunctional, aliphatic polycarbonatepolyols, poly(ε-caprolactone) or polymers of tetrahydrofuran having number average molar masses of greater than 500 g/mol and less than 2100 g/mol.

Preferably used block copolymers of the structure $Y(X_i—H)_n$ comprise more than 50 percent by weight of the blocks $X_i$ described above as being according to the invention and have a number average total molar mass of greater than 1200 g/mol.

Particularly preferred block copolyols comprise less than 50 percent by weight of aliphatic polyester, aliphatic polycarbonatepolyol or poly-THF and more than 50 percent by weight of the blocks $X_i$ described above as being according to the invention and have a number average molar mass of greater than 1200 g/mol. Particularly preferred block copolymers comprise comprise less than 50 percent by weight of aliphatic polycarbonatepolyol, poly(ε-caprolactone) or poly-THF and more than 50 percent by weight of the blocks $X_i$ described above as being according to the invention and have a number average molar mass of greater than 1200 g/mol.

Very particularly preferred block copolymers comprise less than 34 percent by weight of aliphatic polycarbonatepolyol, poly(ε-caprolactone) or poly-THF and more than 66 percent by weight of the blocks $X_i$ described above as being according to the invention and have a number average molar mass of greater than 1950 g/mol and less than 9000 g/mol.

The block copolyols described are prepared by alkylene oxide addition processes. Of industrial importance is firstly the base-catalysed addition reaction of alkylene oxides with starter compounds having Zerewitinoff-active hydrogen atoms $Y(H)_n$; secondly, the the use of double metal cyanide compounds ("DMC catalysts") is becoming increasingly important for carrying out this reaction. Hydrogen bound to N, O or S is designated as Zerewitinoff-active hydrogen (sometimes also only as "active hydrogen") if it gives methane by reaction with methylmagnesium iodide by a process discovered by Zerewitinoff. Typical examples of compounds having Zerewitinoff-active hydrogen are compounds which contain carboxyl, hydroxyl, amino, imino or thiol groups as functional groups. The base-catalysed addition reaction of alkylene oxides, such as, for example, ethylene oxide or propylene oxide, with starter compounds having Zerewitinoff-active hydrogen atoms is effected in the presence of alkali metal hydroxides, but it is also possible to use alkali metal hydrides, alkali metal carboxylates or alkaline earth metal hydroxides. After the addition reaction of the alkylene oxides is complete, the polymerisation-active centres on the polyether chains must be deactivated, for example by neutralisation with dilute mineral acids, such as sulphuric acid or phosphoric acid, and isolation of the resulting salts. In the process according to the invention, DMC catalysts are preferably used. The highly active DMC catalysts which are described, for example, in U.S. Pat. No. 5,470,813, EP-A 700 949, EP-A 743 093, EP-A 761 708, WO 97/40086, WO 98/16310 and WO 00/47649 are particularly preferably used. The highly active DMC catalysts which are described in EP-A 700 949 and, in addition to a double metal cyanide compound (e.g. zinc hexacyanocobaltate(III)) and an organic complex ligand (e.g. tert-butanol), also contain a polyether having a number average molecular weight greater than 500 g/mol are a typical example. Owing to their high activity, these catalysts can be used in such small amounts that further working-up of the polyetherpolyols is not required. The process is described in more detail below. A "starter polyol" used is the OH-functionalised precursor Y which is always present in an amount of less than 50 percent by weight in the block copolymer and onto which alkylene oxide is polymerised, so that a multiblock copolymer is obtained at the end. Preferably used alkylene oxides are ethylene oxide, propylene oxide, butylene oxide and mixtures thereof. The synthesis of the polyether chains by alkoxylation can be carried out, for example, only with a monomeric epoxide or can be effected randomly or blockwise with a plurality of different monomeric epoxides.

Preferred combinations of component a) and b) in the preparation of the matrix polymers are:

A) adducts of butyrolactone, ε-caprolactone and/or methyl-ε-caprolactone with polyetherpolyols having a functionality of 1.8 to 3.1 and having number average molar masses of 200 to 4000 g/mol in combination with isocyanurates, uretdiones, iminooxadiazinediones and/or other oligomers based on HDI. Particularly preferred adducts of ε-caprolactone with poly(tetrahydrofurans) having a functionality of 1.9 to 2.2 and number average molar masses of 500 to 2000 g/mol (in particular 600 to 1400 g/mol), whose number average total molar mass is from 800 to 4500 g/mol, in particular from 1000 to 3000 g/mol, in combination with oligomers, isocyanurates and/or iminooxadiazinediones based on HDI.

B) polyetherpolyols having number average molar masses of 500 to 8500 g/mol and OH functionalities of 1.8 to 3.2, exclusively based on propylene oxide, or random or block copolyols based on propylene oxide and ethylene oxide, the proportion of ethylene oxide being not higher than 60% by weight, in combination with urethanes, allophanates or biurets obtained from aliphatic isocyanate-functional compounds and oligomeric or polymeric isocyanate-reactive compounds having number average molar masses of 200 to 6000 g/mol. Propylene oxide homopolymers having number average molar masses of 1800 to 4500 g/mol and OH functionalities of 1.9 to 2.2 in combination with allophanates obtained from HDI or TMDI and difunctional polyetherpolyols (in particular polypropylene glycols) having number average molar masses of 200 to 2100 g/mol are particularly preferred.

C) polyether block or multiblock copolymers of the formula (I), in which Y is a purely aliphatic polycarbonatepolyol or a polymer of tetrahydrofuran having in each case an OH functionality of 1.8 to 3.1 and a number average molar masses of 400 to 2000 g/mol, n=2, i=1 or 2 and R is methyl or H, having a total number average molar mass of 1950 to 9000 g/mol, preferably of 1950 to 6000 g/mol, in combination with urethanes, allophanates or biurets obtained from aliphatic isocyanate-functional compounds and oligomeric or polymeric isocyanate-reactive compounds having number average molar masses of 200 to 6000 g/mol or in combination with isocyanurates, uretdiones, iminooxadiazinediones and/or other oligomers based on HDI. Polyether block or multiblock copolymers of the formula (I), in which Y is a purely aliphatic polycarbonatepolyol based on 1,4-butanediol and/or 1,6-hexanediol with dimethyl or diethyl carbonate or a polymer of tetrahydrofuran having an OH functionality of 1.8 to 2.2 and a number average molar masses of 600 to 1400 g/mol (in particular up to 1000 g/mol), n=2, i=1 or 2 and R is methyl or H, are particularly preferred, the proportion of the ethylene oxide units, based on the total mass of $X_i$, being not higher than 60% by weight, in combination with allophanates obtained from HDI or TMDI and difunctional polyetherpolyols (in particular polypropylene glycols) having number average molar masses of 200 to 2100 g/mol, in combination with biurets having number average molar masses of 200 to 1400 g/mol (in particular as a mixture with other oligomers of difunctional aliphatic isocyanates), based on aliphatic diamines or polyamines and aliphatic diisocyanates, in particular HDI and TMDI, in combination with urethanes obtained from HDI or TMDI, based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms), having number average molar masses of 200 to 3000 g/mol, particularly preferably of 1000 to 2000 g/mol (in particular as a mixture with other oligomers of difunctional aliphatic isocyanates) or in combination with isocyanurates, iminooxadiazinediones and/or other oligomers based on HDI.

The monofunctional writing monomer (component B)) can preferably have the general formula (II)

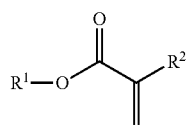

(II)

in which $R^1$, $R^2$ are hydrogen and/or, independently of one another, linear, branched, cyclic or heterocyclic organic radicals which are unsubstituted or optionally also substituted by heteroatoms.

It is particularly preferable if the monofunctional writing monomer has a glass transition temperature $T_G$ of <15° C.

The polyfunctional writing monomer (component B)) may be in particular compounds which have the general formula (III)

(III)

in which n is ≥2 and n is ≤4 and $R^3$, $R^4$ are hydrogen and/or, independently of one another, linear, branched, cyclic or heterocyclic organic radicals which are unsubstituted or optionally also substituted by heteroatoms. It is more preferable if the polyfunctional writing monomer has a refractive index of $n_D^{20} > 1.50$.

Mixtures of compounds, such as α,β-unsaturated acrylate-based carboxylic acid derivatives, such as acrylates, methacrylates, acrylamides, (meth)acrylonitrile, (meth)acrylamide, methacrylic acid, acrylic acid, can be used as writing comonomers essential to the invention. Acrylates and methacrylates are preferred.

In general, esters of acrylic acid or methacrylic acid are designated as acrylates or methacrylates. Examples of acrylates and methacrylates which may be used are methyl acrylate, methyl methacrylate, ethyl acrylate, ethyl methacrylate, ethoxyethyl acrylate, ethoxyethyl methacrylate, n-butyl acrylate, n-butyl methacrylate, tert-butyl acrylate, tert-butyl methacrylate, hexyl acrylate, hexyl methacrylate, 2-ethylhexyl acrylate, 2-ethylhexyl methacrylate, butoxyethyl acrylate, butoxyethyl methacrylate, lauryl acrylate, lauryl methacrylate, isobornyl acrylate, isobornyl methacrylate, phenyl acrylate, phenyl methacrylate, p-chlorophenyl acrylate, p-chlorophenyl methacrylate, p-bromophenyl acrylate, p-bromophenyl methacrylate, 2,4,6-trichlorophenyl acrylate, 2,4,6-trichlorophenyl methacrylate, 2,4,6-tribromophenyl acrylate, 2,4,6-tribromophenyl methacrylate, pentachlorophenyl acrylate, pentachlorophenyl methacrylate, pentabromophenyl acrylate, pentabromophenyl methacrylate, pentabromobenzyl acrylate, pentabromobenzyl methacrylate, phenoxyethyl acrylate, phenoxyethyl methacrylate, phenoxyethoxyethyl acrylate, phenoxyethoxyethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, propane-2,2-diylbis[(2,6-dibromo-4,1-phenylene)oxy(2-{[3,3,3-tris(4-chlorophenyl)propanoyl]oxy}propane-3,1-diyl)oxyethane-2,1-diyl]diacrylate, bisphenol A diacrylate, bisphenol A dimethacrylate, tetrabromobisphenol A diacrylate, tetrabromobisphenol A dimethacrylate and the ethoxylated analogue compounds thereof, N-carbazolyl acrylates, to mention only a selection.

Acrylates and methacrylates having a refractive index $n_D^{20}$ of greater than 1.450 are preferably used. Acrylates which contain at least one aromatic structural unit and have a refractive index $n_D^{20}$ of greater than 1.500 are particularly preferably used. Acrylates and methacrylates based on bisphenol A or derivatives thereof and those acrylates and methacrylates which contain a thioaryl group may be mentioned as particularly suitable examples thereof.

Urethane acrylates may also preferably be used as writing comonomers. Urethane acrylates are understood as meaning compounds having at least one acrylic acid ester group, which additionally have at least one urethane bond. It is known that such compounds can be obtained by reacting a hydroxy-functional acrylic acid ester with an isocyanate-functional compound.

Examples of isocyanates which can be used for this purpose are aromatic, araliphatic, aliphatic and cycloaliphatic di-, tri- or polyisocyanates. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis (4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate, 1,5-naphthylene diisocyanate, triphenylmethane 4,4', 4"-triisocyanate and tris(p-isocyanatophenyl)thiophosphate or derivatives thereof having a urethane, urea, carbodiimide, acylurea, isocyanurate, allophanate, biuret, oxadiazinetrione, uretdione or iminooxadiazinedione structure and mixtures thereof. Aromatic or araliphatic di-, tri- or polyisocyanates are preferred.

Suitable hydroxy-functional acrylates or methacrylates for the preparation of urethane acrylates are, for example, compounds such as 2-hydroxyethyl(meth)acrylate, polyethylene oxide mono(meth)acrylates, polypropylene oxide mono(meth)acrylates, polyalkylene oxide mono(meth)-acrylates, poly($\epsilon$-caprolactone)mono(meth)acrylates, such as, for example, Tone® M100 (Dow, Schwalbach, Germany), 2-hydroxypropyl(meth)acrylate, 4-hydroxybutyl(meth)acrylate, 3-hydroxy-2,2-dimethylpropyl(meth)acrylate, hydroxypropyl(meth)acrylate, 2-hydroxy-3-phenoxypropyl acrylate, the hydroxy-functional mono-, di- or tetraacrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or industrial mixtures thereof. 2-Hydroxyethyl acrylate, hydroxypropyl acrylate, 4-hydroxybutyl acrylate and poly($\epsilon$-caprolactone)mono(meth)acrylates are preferred. In addition, are suitable as isocyanate-reactive oligomeric or polymeric unsaturated compounds containing acrylate and/or methacrylate groups, alone or in combination with the above-mentioned monomeric compounds. The epoxy(meth)acrylates known per se, containing hydroxyl groups and having OH contents of 20 to 300 mg KOH/g or polyurethane(meth)acrylates containing hydroxyl groups and having OH contents of 20 to 300 mg KOH/g or acrylated polyacrylates having OH contents of 20 to 300 mg KOH/g and mixtures thereof with one another and mixtures with unsaturated polyesters containing hydroxyl groups and mixtures with polyester(meth)acrylates or mixtures of unsaturated polyesters containing hydroxyl groups with polyester(meth)acrylates can also be used. Epoxy acrylates containing hydroxyl groups and having a defined hydroxy functionality are preferred. Epoxy (meth)acrylates containing hydroxyl groups are based in particular on reaction products of acrylic acid and/or methacrylic acid with epoxides (glycidyl compounds) of monomeric, oligomeric or polymeric bisphenol A, bisphenol F, hexanediol and/or butanediol or the ethoxylated and/or propoxylated derivatives thereof. Epoxy acrylates having a defined functionality, as can be obtained from the known reaction of acrylic acid and/or methacrylic acid and glycidyl(meth)acrylate, are furthermore preferred.

Mixtures of (meth)acrylates and/or urethane(meth)acrylates are preferably used, particularly preferably (meth)acrylates and/or urethane(meth)acrylates which have at least one aromatic structural unit.

Particularly preferred compounds which are to be used as writing comonomers are mixtures of urethane acrylates and urethane methacrylates based on aromatic isocyanates and 2-hydroxyethyl acrylate, hydroxypropyl acrylate, 4-hydroxybutyl acrylate, polyethylene oxide mono(meth)acrylate, polypropylene oxide mono(meth)acrylate, polyalkylene oxide mono(meth)acrylate and poly($\epsilon$-caprolactone)mono(meth)acrylates.

In a very particularly preferred embodiment, the mixtures of the adducts of aromatic triisocyanates (very particularly preferably tris(4-phenylisocyanato)thiophosphate or trimers of aromatic diisocyanates such as toluene diisocyanate) with hydroxyethyl acrylate, hydroxypropyl acrylate, 4-hydroxybutyl acrylate, together with the adducts of 3-thiomethylphenyl isocyanate with hydroxyethyl acrylate, hydroxypropyl acrylate, 4-hydroxybutyl acrylate, are used as writing comonomers (as described in the applications WO 2008/125229 A1 and in the non-prior-published application EP 09009651.2).

Furthermore, the use of glycidyl ether acrylate urethanes as writing monomers is preferred. These obey the general formula (IVa) or (IVb) or mixtures of (IVa) and (IVb)

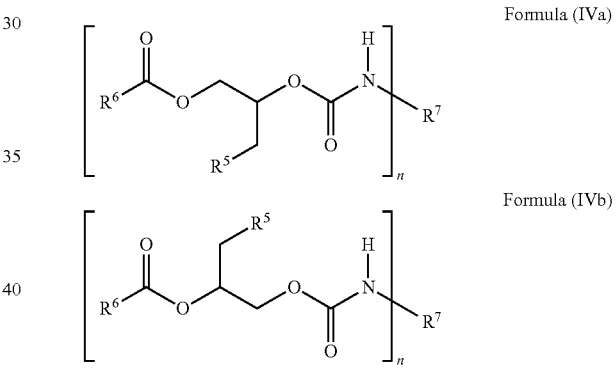

Formula (IVa)

Formula (IVb)

in which n is a natural number from 2 to 6, $R^5$ is a mono- or polynuclear organic radical containing aromatic groups and having 4 to 36 carbon atoms, $R^6$ is an olefinically unsaturated radical having 3 to 30 carbon atoms and $R^7$ is an organic radical derived from an aliphatic or aromatic di- or polyisocyanate and having 2 to 30 carbon atoms.

The unsaturated glycidyl ether acrylate urethanes of the formula IVa or IVb can be prepared in a 2-stage synthesis. In the first reaction, an unsaturated carboxylic acid is reacted with an epoxide, a mixture of two alcohols being formed. In a second reaction step, this alcohol mixture is urethanized by means of a di- or polyisocyanate $R^7(NCO)_n$ having a functionality of n to give the glycidyl ether acrylate urethane (as described in the non-prior-published application EP 09002180.9). Preferably methacrylic acid and acrylic acid or derivatives thereof will be used as epoxides, preferably aromatic epoxides, such as phenyl, dibromophenyl, naphthyl or biphenyl glycidyl ether, and toluene diisocyanate (TDI), hexamethylene diisocyanate (HDI) or triisocyanatononane (TIN) is preferably used as the isocyanate component.

In a very particularly preferred embodiment, the combinations of (acrylic acid, biphenyl glycidyl ether and TDI), (acrylic acid, phenyl glycidyl ether and TDI) and (acrylic acid, biphenyl glycidyl ether and HDI) are used.

Furthermore, specific methacrylates of the general formulae Va and Vb can also be used

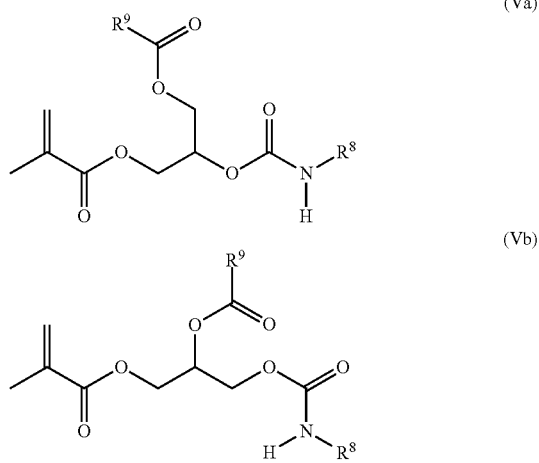

in which $R^8$ and $R^9$, independently of one another, are substituted phenyl radicals, substituted and/or unsubstituted naphthyl radicals. Preferably, $R^8$ and/or $R^9$ may comprise 6-24 C atoms, 0-5 S atoms and 0-5 halogen atoms.

According to a preferred embodiment, $R^8$ and/or $R^9$ may be substituted by thioether groups, phenyl groups and/or halogen atoms.

It is very particularly preferred if $R^8$ and/or $R^9$ are naphthyl, 3-methylthiophenyl, 2-, 3-, 4-biphenyl, 2-bromophenyl.

The preparation of the methacrylates is effected in a 2-stage synthesis. In the first reaction, an acid $R^9$—COOH is reacted with glycidyl methacrylate, a mixture of two alcohols being formed. A second reaction step, the alcohol mixture is urethanized with a monoisocyanate $R^8$—NCO to give the methacrylate mixture.

In a very particularly preferred embodiment, the combinations of (glycidyl methacrylate, naphthoic acid and 3-thiomethylphenyl isocyanate) are used.

One or more photoinitiators are used as component C). These are usually initiators which can be activated by actinic radiation and initiate polymerisation of the corresponding polymerisable groups. Photoinitiators are commercially sold compounds known per se, a distinction being made between monomolecular (type I) and bimolecular (type II) initiators. Furthermore, depending on the chemical nature, these initiators are used for free radical, anionic (or), cationic (or mixed) forms of the abovementioned polymerisations.

(Type I) systems for free radical photopolymerisation are, for example, aromatic ketone compounds, e.g. benzophenones, in combination with tertiary amines, alkylbenzophenones, 4,4'-bis(dimethylamino)benzophenone (Michler's ketone), anthrone and halogenated benzophenones or mixtures of said types. More suitable are (type II) initiators, such as benzoin and its derivatives, benzil ketals, acylphosphine oxides, e.g. 2,4,6-trimethylbenzoyldiphenylphosphine oxide, bisacylophosphine oxides, phenylglyoxylic acid esters, camphorquinone, alpha-aminoalkylphenones, alpha,alpha-dialkoxyacetophenones, 1-[4-(phenylthio)phenyl]octane-1,2-dione 2-(O-benzoyloxime), differently substituted hexarylbisimidazoles (HABI), with suitable coinitiators, such as, for example, mercaptobenzoxazole and alpha-hydroxyalkylphenones. The photoinitiator systems described in EP-A 0223587 and consisting of a mixture of an ammonium arylborate and one or more dyes can also be used as a photoinitiator. For example, tetrabutylammonium triphenylhexylborate, tetrabutylammonium triphenylbutylborate, tetrabutylammonium trinaphthylbutylborate, tetramethylammonium triphenylbenzylborate, tetra(n-hexyl) ammonium(sec-butyl)triphenylborate, 1-methyl-3-octylimidazolium dipentyldiphenylborate, tetrabutylammonium tris (4-tert-butyl)phenylbutylborate, tetrabutylammonium tris(3-fluorophenyl)-hexylborate and tetrabutylammonium tris(3-chloro-4-methylphenyl)hexylborate are suitable as an ammonium arylborate. Suitable dyes are, for example, new methylene blue, thionine, basic yellow, pinacynol chloride, rhodamine 6G, gallocyanine, ethyl violet, Victoria blue R, celestine blue, quinaldine red, crystal violet, brilliant green, astrazone orange G, darrow red, pyronine Y, basic red 29, pyrillium I, safranine O, cyanine and methylene blue, azure A (Cunningham et al., RadTech '98 North America UV/EB Conference Proceedings, Chicago, Apr. 19-22, 1998).

The photoinitiators used for the anionic polymerisation are as a rule (type I) systems and are derived from transition metal complexes of the first series. Here are chromium salts, such as, for example, trans-Cr(NH$_3$)$_2$(NCS)$_4$— (Kutal et al, Macromolecules 1991, 24, 6872) or ferrocenyl compounds (Yamaguchi et al. Macromolecules 2000, 33, 1152). A further possibility of anionic polymerisation consists in the use of dyes, such as crystal violet leuconitrile or malchite green leuconitrile, which can polymerise cyanoacrylates by photolytic decomposition (Neckers et al. Macromolecules 2000, 33, 7761). However, the chromophore is incorporated into the polymer thereby so that the resulting polymers are coloured throughout.

The photoinitiators used for the cationic polymerisation substantially comprise three classes: aryldiazonium salts, onium salts (here especially: iodonium, sulphonium and selenonium salts) and organometallic compounds. On irradiation both in the presence and in the absence of a hydrogen donor, phenyldiazonium salts can produce a cation that initiates the polymerisation. The efficiency of the overall system is determined by the nature of the counterion used for the diazonium compound. The not very reactive but very expensive SbF6-, AsF6- or PF6- are preferred here. These compounds are as a rule not very suitable for use in the coating of thin films since the surface quality is reduced (pinholes) the the nitrogen liberated after the exposure (Li et al., Polymeric Materials Science and Engineering, 2001, 84, 139). Onium salts, especially sulphonium and iodonium salts, are very widely used and also commercially available in a variety of forms. The photochemistry of these compounds has been investigated over a long time. The iodonium salts decompose, initially homolytically, after excitation and thus produce a free radical and a radical anion which is stabilised by H abstraction and liberates a proton and then initiates the cationic polymerisation (Dektar et al. J. Org. Chem. 1990, 55, 639; J. Org. Chem., 1991, 56. 1838). This mechanism permits the use of iodonium salts also for free radical photopolymerisation. Here too, the choice of the counterion is of major importance; SbF$_6^-$, AsF$_6^-$ or PF$_6^-$ is likewise preferred. In this structure class, the choice of the substitution of the aromatic otherwise entirely free and determined substantially by the availability of suitable starting building blocks for the synthesis. The sulphonium salts are compounds which decompose in according to Norrish(II) (Crivello et al., Macromolecules, 2000, 33, 825). In the case of sulphonium salts, too, the choice of the counterion is of critical importance, which manifests itself substantially in the curing rate of the polymers. The best results are achieved as a rule with SbF$_6$ salts. Since the self-absorption of iodonium and sulphonium salts is at <300 nm, these compounds must be appropriately sensitized for the photopolymerisation with near UV or short-wave visible light. This is effected by the use of more highly absorbing aromatics, such as, for example, anthracene and derivatives (Gu et al., Am. Chem. Soc. Polymer Preprints, 2000, 41 (2), 1266) or phenothiazine or derivatives thereof (Hua et al, Macromolecules 2001, 34, 2488-2494).

It may be advantageous also to use mixtures of these compounds. Depending on the radiation source used for the curing, type and concentration of photoinitiator must be adapted in a manner known to a person skilled in the art. More details are described, for example, in P. K. T. Oldring (Ed.), Chemistry & Technology of UV & EB Formulations For Coatings, Inks & Paints, Vol. 3, 1991, SITA Technology, London, pages 61-328.

Preferred photoinitiators are mixtures of tetrabutylammonium triphenylhexylborate, tetrabutylammonium triphenylbutylborate, tetrabutylammonium trinaphthylbutylborate, tetrabutylammonium tris(4-tert-butyl)phenylbutylborate, tetrabutylammonium tris(3-fluorophenyl)-hexylborate and tetrabutylammonium tris(3-chloro-4-methylphenyl)hexylborate with dyes, such as, for example, astrazone orange G, methylene blue, new methylene blue, azure A, pyrillium I, safranine O, cyanine, gallocyanine, brilliant green, crystal violet, ethyl violet and thionine.

The photoinitiator system used can preferably comprise an anionic, cationic or neutral dye and a coinitiator.

The photopolymer formulation may additionally contain a non-photopolymerisable component D) as a plasticizer. The plasticizer can preferably be chosen so that the refractive index of the plasticizer is at least 0.05 unit less than the refractive index of the matrix polymers if both writing monomers have higher refractive indices than the matrix polymers, and the refractive index of the plasticizer is at least 0.05 unit greater than the refractive index of the matrix polymers if both writing monomers have refractive indices less than the refractive index of the matrix polymers.

Plasticizers which may be used are in particular urethanes of the general formula (VI)

(VI)

in which n is ≥1 and n is ≤8 and R$^{10}$, R$^{11}$, R$^{12}$ are hydrogen and/or, independently of one another, linear, branched, cyclic or heterocyclic organic radicals which are unsubstituted or optionally also substituted by heteroatoms, preferably at least one of the radicals R$^{10}$, R$^{11}$, R$^{12}$ being substituted by at least one fluorine atom and particularly preferably R$^{10}$ being an organic radical having at least one fluorine atom.

Further constituents E) of the photopolymer formulation may be: free radical stabilisers, optionally catalysts and other auxiliaries and additives.

Inhibitors and antioxidants as described, for example, in "Methoden der organischen Chemie [Methods of Organic Chemistry]" (Houben-Weyl), 4$^{th}$ edition, Volume XIV/1, page 433 et seq., Georg Thieme Verlag, Stuttgart 1961, are suitable as examples of free radical stabilisers. Suitable classes of substances are, for example, phenols, such as, for example, 2,6-di-tert-butyl-4-methylphenol, cresols, hydroquinones, benzyl alcohols, such as, for example, benzhydrol, optionally also quinones, such as, for example, 2,5-di-tert-butylquinone, optionally also aromatic amines, such as diisopropylamine or phenothiazine.

2,6-Di-tert-butyl-4-methylphenol, phenothiazine, p-methoxyphenol, 2-methoxy-p-hydroquinone and benzhydrol are preferred.

Optionally, one or more catalysts may be used. These are catalysts for accelerating the urethane formation. Known catalysts for this purpose are, for example, tin octanoate, zinc octanoate, dibutyltin dilaurate, dimethylbis[(1-oxoneodecyl)oxy]stannane, dimethyltin dicarboxylate, zirconium bis(ethylhexanoate), zirconium acetylacetonate or tertiary amines, such as, for example, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido (1,2-a)pyrimidine.

Dibutyltin dilaurate, dimethylbis[(1-oxoneodecyl)oxy]stannane, dimethyltin dicarboxylate, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine are preferred.

Of course, further auxiliaries and additives can optionally be used. These may be, for example, additives customary in the area of coating technology, such as solvents, plasticizers, levelling agents or adhesion promoters. It may also be advantageous simultaneously to use a plurality of additives of one type. Of course, it may also be advantageous to use a plurality of additives of a plurality of types.

According to a further preferred embodiment, it is intended that the refractive index contrast Δn of individual exposed, holographic media varies by less than 55% with different proportions of monofunctional and polyfunctional writing monomers, the variation being calculated as follows: (Δn$_{max}$−Δn$_{min}$)/Δn$_{min}$·100%.

It is also possible to bond a layer of the photopolymer formulation in step ii) to a substrate. In addition, the layer of the photopolymer formulation can be bonded to a further substrate.

Preferably, the coating and the substrate or substrates can be bonded to one another by lamination or adhesive bonding.

The invention furthermore relates to an exposed holographic medium that is obtainable by the process according to the invention.

EXAMPLES

The invention is explained in more detail below with reference to examples.

Designations which are Used Below:

Photopolymer formulations comprising:

three-dimensionally crosslinked organic polymers A) as matrix. Particularly preferred three-dimensionally crosslinked organic polymers are those which are composed of an isocyanate component a)

and an isocyanate-reactive component b) as precursors and are crosslinked with the aid of a catalyst component E) which as a rule is added in solution, compounds B) which have groups reacting under the action of actinic radiation with ethylenically unsaturated compounds with polymerisation (radiation-curing groups) and are present in dissolved or disperse form in this matrix, at least one photoinitiator C), optionally a non-photopolymerisable component D), optionally catalysts, free radical stabilisers, solvents, additives and other auxiliaries and/or additives E), F designates the photopolymer formulation with 0.1% by weight of Darocur TPO as a UV initiator C4), which is used for determining the UV modulus $G_{UV}$, M designates the holographic medium comprising the corresponding photopolymer formulation F but in which Darocure TPO was replaced by the corresponding photoinitiator C) for the visible range.

Methods of Measurement:

Unless noted otherwise, all stated percentages are based on percent by weight.

Measurement of the Refractive Indices of the Photopolymerisable Writing Monomers B) and of the Non-Photopolymerisable Components D)

The refractive index n as a function of the wavelength of the samples were determined from the transmission and reflection spectra. For this purpose, about 100-300 nm thick films of the samples were applied by spin coating to quartz glass substrates from dilute solution in butyl acetate. The transmission and reflection spectrum of this layer packet was measured with a spectrometer from STEAG ETA-Optik, CD-Measurement System ETA-RT, and the layer thickness and spectral curve of n were then fitted to the measured transmission and reflection spectra. This is effected using the internal software of the spectrometer and additionally requires the refractive index data of the quartz glass substrate, which were determined beforehand in a blank measurement. The refractive indices $n_{Mo}$ for the photopolymerisable monomers B) or $n_{CA}$ for the non-polymerisable components D) are based on the wavelength of a sodium vapour lamp of 589 nm and therefore corresponds to $n_D^{20}$. The refractive indices obtained are shown in Table 1.

Measurement of the Refractive Indices of the Matrix Component A), Based on a Polymeric Urethane Network For the production of the photopolymer matrices for determining the refractive index $n_{Ma}$, the isocyanate-reactive component b) is optionally heated to 60° C. Thereafter, the isocyanate component a) is added and mixing is effected in a Speedmixer (from Hauschild) for 1 minute. Thereafter, a solution of component E) is added and mixing is effected in a Speedmixer again for 1 minute. The solution of component E) is 10 percent by weight in n-ethylpyrrolidone. The correspondingly used amounts of solution and the refractive indices obtained are shown in Table 1. The still liquid formulation is applied by knifecoating in the desired thickness to glass plates.

The matrix based on a polymeric network was prepared as an about 500 μm to 1000 μm thick layer on a glass substrate. The refractive index $n_{Ma}$ at the wavelength of the sodium vapour lamp of 589 nm was determined on this sample by means of an Abbe refractometer analogously to DIN 51423-2 and thus corresponds to $n_D^{20}$.

Measurement of the Glass Transition Temperatures $T_G$ of the Various Components For determining the glass transition temperature $T_G$, ~10 mg of the substance were weighed into an aluminium crucible, which is closed with a perforated cover. The glass transition temperature is then determined on the samples prepared in this manner, using a differential scanning calorimeter DSC822°/400 from Mettler-Toledo. Three heating cycles with a heating rate of 20 K/min are run. The start and end temperature of the first cycle is −100° C. and 80° C., respectively. The start and end temperatures of the second and third cycles are −100° C. and 150° C., respectively. The corresponding cooling rates are 50 K/min. The oven and the sample of the calorimeter are flushed with a nitrogen stream having a flow rate of 20 ml/min. The glass transition temperature in the $3^{rd}$ heating cycle is determined as $T_G$ of the sample.

Measurement of the Holographic Properties DE and Δn of the Holographic Media by Means of Two-Beam Interference in Reflection Arrangement The media produced as described in the section "Production of the holographic media based on photopolymer formulation with photoinitiator for determining the performance parameters DE and Δn" were then tested with regard to their holographic properties by means of a measuring arrangement according to FIG. 1, as follows:

The beam of an He—Ne laser (emission wavelength 633 nm) was converted with the aid of the spatial filter (SF) and together with the collimation lens (CL) into a parallel homogeneous beam. The final cross sections of the signal and reference beam are established by the iris diaphragms (I). The diameter of the iris diaphragm opening is 0.4 cm. The polarisation-dependent beam splitters (PBS) split the laser beam into two coherent equally polarised beams. Via the λ/2 plates, the power of the reference beam was adjusted to 0.5 mW and the power of the signal beam to 0.65 mW. The powers were determined using the semiconductor detectors (D) with sample removed. The angle of incidence ($\alpha_0$) of the reference beam is −21.8° and the angle of incidence ($\beta_0$) of the signal beam is 41.8°. The angles are measured starting from the sample normal to the beam direction. According to FIG. 1, $\alpha_0$ therefore has a negative sign and $\beta_0$ a positive sign. At the location of the sample (medium), the interference field of the two overlapping beams produced a grating of light and dark strips which are perpendicular to the angle bisector of the two beams incident on the sample (reflection hologram). The strip spacing Λ, also referred to as grating period, in the medium is ~225 nm (the refractive index of the medium assumed to be 1.504).

FIG. 1 shows the geometry of a Holographic Media Tester (HMT) at λ=633 nm (He—Ne laser): M=mirror, S=shutter, SF=spatial filter, CL=collimator lens, λ/2=λ/2 plate, PBS=polarisation-sensitive beam splitter, D=detector, I=iris diaphragm, $\alpha_0$=−21.8°, $\beta_0$=41.8° are the angles of incidence of the coherent beams, measured outside the sample (outside the medium). RD=reference direction of the turntable.

The diffraction efficiency (DE) of the media were measured using a holographic experimental setup as shown in FIG. 1.

Holograms were recorded in the medium in the following manner:
both shutters (S) are opened for the exposure time t.
thereafter, with closed shutters (S), the medium was allowed a time of 5 minutes for diffusion of the still unpolymerised writing monomers.

The holograms recorded were now read in the following manner. The shutter of the signal beam remained closed. The shutter of the reference beam was opened. The iris diaphragm of the reference beam was closed to a diameter of <1 mm. This ensured that the beam was always completely in the previously recorded hologram for all angles of rotation ($\Omega$) of the medium. The turntable, under computer control, covered the angle range from $\Omega_{min}$ to $\Omega_{max}$ with an angle step width of 0.05°. $\Omega$ is measured from the sample normal to the reference direction of the turntable. The reference direction of the turntable is obtained when, during recording of the hologram, the angle of incidence of the reference beam and the signal beam are of the same magnitude, i.e. $\alpha_0=-31.8°$ and $\beta_0=31.8°$. Then, $\Omega_{recording}$ is 0°. For $\alpha_0=-21.8°$ and $\beta_0=41.8°$, $\Omega_{recording}$ is therefore 10°. In general, the following is true for the interference field during recording of the hologram:

$$\alpha_0 = \theta_0 + \Omega_{recording}.$$

$\theta_0$ is the semiangle in the laboratory system outside the medium, and the following is true during recording of the hologram:

$$\theta_0 = \frac{\alpha_0 - \beta_0}{2}.$$

In this case, $\theta_0$ is therefore $-31.8°$. At each angle of rotation $\Omega$ approached, the powers of the beam transmitted in the zeroth order were measured by means of the corresponding detector D and the powers of the beam diffracted in the first order were measured by means of the detector D. The diffraction efficiency was obtained at each angle $\Omega$ approached as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency $\eta$ as a function of the angle of rotation $\Omega$ of the recorded hologram) was measured and was stored in a computer. In addition, the intensity transmitted in the zeroth order was also plotted against the angle of rotation $\Omega$ and stored in a computer.

The maximum diffraction efficiency (DE=$\eta_{max}$) of the hologram, i.e. its peak value, was determined at $\Omega_{reconstruction}$. It may have been necessary for this purpose to change the position of the detector of the diffracted beam in order to determine this maximum value.

The refractive index contrast $\Delta n$ and the thickness d of the photopolymer layer was now determined by means of the coupled wave theory (cf. H. Kogelnik, The Bell System Technical Journal, Volume 48, November 1969, Number 9, page 2909-page 2947) from the measured Bragg curve and the variation of the transmitted intensity of the functional angle. It should be noted that, owing to the thickness shrinkage occurring as a result of the photopolymerisation, the strip spacing $\Lambda'$ of the hologram and the orientation of the strips (slant) may differ from the strip spacing $\Lambda$ of the interference pattern and the orientation thereof. Accordingly, the angle $\alpha_0'$ or the corresponding angle of the turntable $\Omega_{reconstruction}$ at which maximum diffraction efficiency is achieved will also differ from $\alpha_0$ or from the corresponding $\Omega_{recording}$ respectively. As a result, the Bragg condition changes. This change is taken into account in the evaluation method. The evaluation method is described below:

All geometrical quantities which relate to the hologram recorded and not to the interference pattern are shown as quantities represented by dashed lines.

According to Kogelnik, the following is true for the Bragg curve $\eta(\Omega)$ of a reflection hologram:

$$\eta = \begin{cases} \dfrac{1}{1 - \dfrac{1-(\xi/\nu)^2}{\sin^2\left(\sqrt{\xi^2 - \nu^2}\right)}}, & \text{for } \nu^2 - \xi^2 < 0 \\[2ex] \dfrac{1}{1 + \dfrac{1-(\xi/\nu)^2}{\sinh^2\left(\sqrt{\nu^2 - \xi^2}\right)}}, & \text{for } \nu^2 - \xi^2 \geq 0 \end{cases}$$

with:

$$\nu = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

During reading of the hologram ("reconstruction"), the following is true, as described analogously above:

$$\theta'_0 = \theta_0 + \Omega$$

$$\sin(\theta'_0) = n \cdot \sin(\theta')$$

Under the Bragg condition, the "dephasing" DP is 0. Accordingly:

$$\alpha'_0 = \theta_0 + \Omega_{reconstruction}$$

$$\sin(\alpha'_0) = n \cdot \sin(\alpha')$$

The still unknown angle β' can be determined from the comparison of the Bragg condition of the interference field on recording the hologram and the Bragg condition on reading the hologram, assuming that only thickness shrinkage takes place. The following is then true:

$$\sin(\beta') = \frac{1}{n} \cdot [\sin(\alpha_0) + \sin(\beta_0) - \sin(\theta_0 + \Omega_{reconstruction})]$$

ν is the grating thickness, ξ is the detuning parameter and ψ' is the orientation (slant) of the refractive index grating which was recorded. α' and β' correspond to the angles $\alpha_0$ and $\beta_0$ of the interference field during recording of the hologram, but measured in the medium and applicable to the grating of the hologram (after thickness shrinkage). n is the average refractive index of the photopolymer and was set at 1.504. λ is the wavelength of the laser light in vacuo.

The maximum diffraction efficiency (DE=$\eta_{max}$) is then obtained for ξ=0 as:

$$DE = \tanh^2(\nu) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 2:
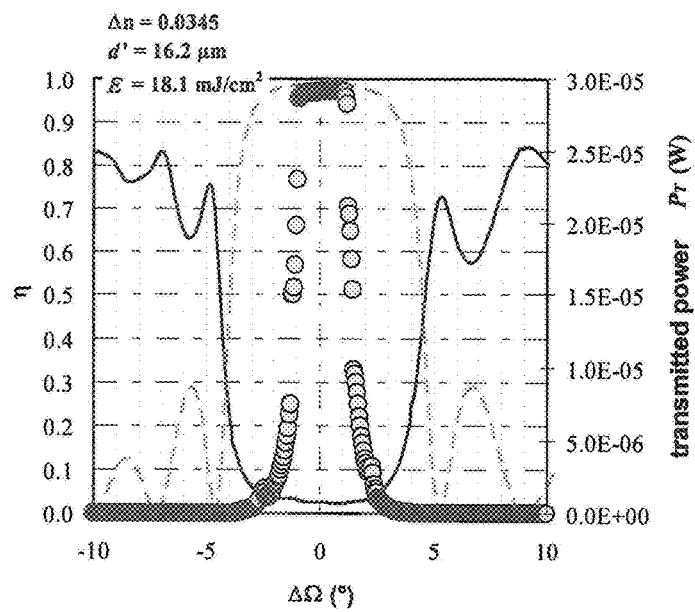
FIG. 2 illustrates a graph showing the measurement data of the diffraction efficiency, the theoretical Bragg curve and the transmitted intensity, plotted against the angle detuning.

FIG. 2 shows the measured transmitted power $P_T$ (right y axis) as a solid line, plotted against the angle detuning ΔΩ, the measured diffraction efficiency η (left y axis) as solid circles, plotted against the angle detuning ΔΩ (if permitted by the finite size of the detector), and the fit of the Kogelnik theory as a dashed line (left y axis).

The measurement data of the diffraction efficiency, the theoretical Bragg curve and the transmitted intensity, as shown in FIG. 2, are plotted against the corrected angle of rotation $\Delta\Omega \equiv \Omega_{reconstruction} - \Omega = \alpha'_0 - \theta'_0$, also referred to as angle detuning.

Since DE is known, the shape of the theoretical Bragg curve according to Kogelnik is determined only by the thickness d' of the photopolymer layer. Δn is subsequently corrected via DE for a given thickness d' so that measurement and theory of DE always agree. d' is now adapted until the angle positions of the first secondary minima of the theoretical Bragg curve agree with the angle positions of the first secondary maxima of the transmitted intensity and additionally the full width at half maximum (FWHM) of the theoretical Bragg curve and for the transmitted intensity agree.

Since the direction in which a reflection hologram concomitantly rotates on reconstruction by means of an Ω scan, but the detector for the diffracted light can detect only a finite angle range, the Bragg curve of broad holograms (small d') is not completely detected in an Ω scan, but only the central region, with suitable detector positioning. That shape of the transmitted intensity which is complementary to the Bragg curve is therefore additionally used for adapting the layer thickness d'.

FIG. 2 shows the plot of the Bragg curve η according to the coupled wave theory (dashed line), of the measured diffraction efficiency (solid circles) and of the transmitted power (black solid line) against the angle detuning ΔΩ.

For a formulation, this procedure was possibly repeated several times for different exposure times t on different media in order to determine the average energy dose of the incident laser beam at which DE reaches the saturation value during recording of the hologram. The average energy dose E is obtained from the powers of the two part-beams coordinated with the angles $\alpha_0$ and $\beta_0$ (reference beam with $P_r$=0.50 mW and signal beam with $P_s$=0.65 mW), the exposure time t and the diameter of the iris diaphragm (0.4 cm), as follows:

$$E(mJ/cm^2) = \frac{2 \cdot [P_r + P_s] \cdot t(s)}{\pi \cdot 0.4^2 cm^2}$$

The powers of the part-beams were adapted so that the same power density is achieved in the medium at the angles $\alpha_0$ and $\beta_0$ used.

As an alternative, a test equivalent to the setup shown in FIG. 1 was also carried out using a green laser having the emission wavelength λ in vacuo of 532 nm. Here, $\alpha_0$=−11.5° and $\beta_0$=33.5° and $P_r$=1.84 mW and $P_s$=2.16 mW.

Measurement of the Modulus $G_{UV}$ of the Photopolymers After UV Crosslinking by Means of an Oscillation Rheometer in the Context of the Present Invention The still liquid formulation (F) is then introduced into the plate-plate measuring system of a rheometer (from Anton Paar Physica model MCR 301, equipped with the oven model CTD 450L+R+L+PP/GL, equipped with a transparent base plate in the plate-plate measuring system, which was preheated to 50° C.). The curing of the matrix of the photopolymer formulation is then measured, initially as a function of time, under the following conditions:

plate spacing 250 µm, plate diameter 12 mm.

oscillation measuring mode at a constant angular frequency $\omega_0$ of 62.8 rad/s and a controlled logarithmic deformation amplitude ramp of 10%-0.01%.

temperature 50° C., normal force regulation set at 0 Newton.

recording of the storage modulus G' over the measuring time for at least 2 hours or until a constant value of G' was reached. This value is referred to as $G_0$.

The UV curing of the photopolymer is with a 100 W high-pressure mercury vapour lamp OmniCure Series 1000, equipped with standard filter 320 nm-500 nm.

Exposure of the photopolymer through the transparent lower plate to a mercury vapour lamp. The aperture of the lamp exit is adjusted so that the power density at the exit of the waveguide (measured with EXFO Radiometer R2000 supplied), which is introduced into the measuring chamber and leads the light to the transparent glass plate, is 600 mW/cm².

Oscillation measuring mode at a constant angular frequency $\omega_0$ of 62.8 rad/s and a controlled logarithmic deformation amplitude ramp deformation amplitude of 0.01%-0.001%.

Temperature 50° C., normal force regulation set at 0 Newton.

Recording of the storage modulus G' during the UV exposure over the measuring time for at least 15 minutes or until a constant value of G' was reached. This value is taken as $G_{UV}$.

Figure 3:
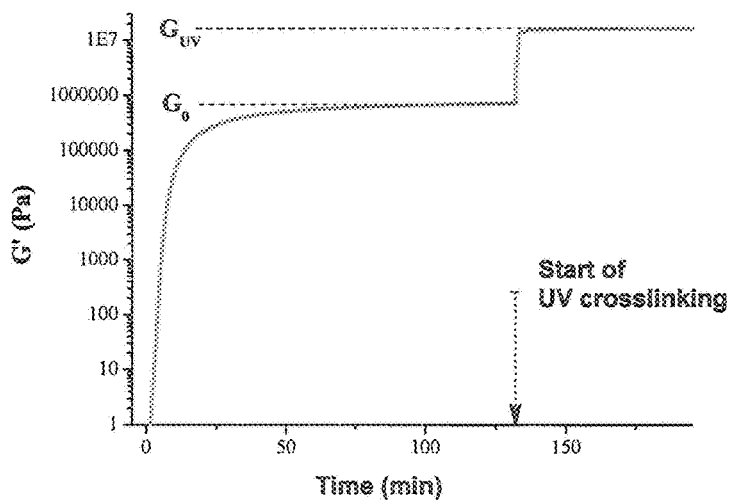
FIG. 3 illustrates an example measurement curve of the curing of the matrix network (left) and of the subsequent UV crosslinking (right) on the basis of the storage modulus G'.

An example of a typical measured curve is to be found in FIG. 3. FIG. 3 shows the curve of the curing of the matrix network (left) and of the subsequent UV crosslinking (right) on the basis of the storage modulus G'.

Description of the Formulation Constituents Used in the Examples:

Isocyanates Used (Component a))

Desmodur® XP 2599 is a product of Bayer MaterialScience AG, Leverkusen, Germany, full allophanate of hexane diisocyanate on Acclaim 4200, NCO content: 5.6-6.4% (component a1)).

Desmodur® XP 2747 is a product of Bayer MaterialScience AG, Leverkusen, Germany, full allophanate of hexane diisocyanate on polypropylene glycol having a number average molar mass of about 280 g/mol, NCO content: 16.5-17.3% (component a2)).

Desmodur® XP 2410 is a product of Bayer MaterialScience AG, Leverkusen, Germany, hexane diisocyanate-based polyisocyanate, proportion of iminooxadiazinedione at least 30%, NCO content: 23.5% (component a3)).

Desmodur® XP 2580 is a product of Bayer MaterialScience AG, Leverkusen, Germany, aliphatic polyisocyanate based on hexane diisocyanate, NCO content about 20% (component a4)).

Isocyanate-Reactive Components Used (Component b))

Acclaim® 4200 is a commercial product of Bayer MaterialScience AG, Leverkusen, Germany, polypropylene oxide having a number average molar mass of 4000 g/mol (polyol b1)).

Polyol b2) is an experimental product of Bayer MaterialScience AG, Leverkusen, Germany, the preparation is described below.

Preparation of Polyol b2):

2475 g of Terathane® 650 (polytetrahydrofuran having a molar mass of 650 g/mol), a product of BASF SE, Ludwigshafen, Germany, were weighed into a 20 l reaction vessel equipped with a stirrer and 452.6 mg of DMC catalyst were added. Heating to 105° C. was then effected with stirring at about 70 rpm. By applying a vacuum and eliminating the vacuum with nitrogen three times, air was exchanged for nitrogen. After the stirrer speed had been increased to 300 rpm, nitrogen was passed through the mixture from below for 57 minutes with the vacuum pump running and at a pressure of about 0.1 bar. Thereafter, a pressure of 0.5 bar was established by means of nitrogen and 100 g of ethylene oxide (EO) and 150 g of PO were passed in simultaneously at the start of the polymerisation. The pressure increased to 2.07 bar thereby. After 10 minutes, the pressure had dropped again to 0.68 bar, and a further 5.116 kg of EO and 7.558 kg of PO as a mixture were passed in over a period of 1 h 53 min at 2.34 bar. 31 minutes after the end of the epoxide metering, a vacuum was applied at a residual pressure of 2.16 bar and complete devolatilisation was effected. The product was stabilised by addition of 7.5 g of Irganox 1076 and obtained as a slightly turbid (TE(F) number 330), viscous liquid (OH number 27.1 mg KOH/g, viscosity at 25° C.: 1636 mPas).

Polyol b3) is an experimental product of Bayer MaterialScience AG, Leverkusen, Germany, block copolymer of Terathane® 1000 (polytetrahydrofuran polyetherpolyol having a molar mass of 1000 g/mol), a product of BASF SE, Ludwigshafen, Germany, and ε-caprolactone, the preparation is described below.

Preparation of Polyol b3):

In a 1 l flask, 0.18 g of tin octanoate, 374.8 g of ε-caprolactone and 374.8 g of a difunctional polytetrahydrofuran polyetherpolyol (equivalent weight 500 g/mol OH) were initially introduced and heated to 120° C. and kept at this temperature until the solids content (proportion of the non-volatile constituents) was 99.5% by weight or higher. Thereafter, cooling was effected and the product was obtained as a waxy solid.

Polyol b4) is an experimental product of Bayer MaterialScience AG, Leverkusen, Germany, the preparation is described below.

Preparation of Polyol b4):

2465 g of Terathane® 650 were weighed into a 20 l reaction vessel equipped with a stirrer and 450.5 mg of DMC catalyst were added. Heating to 105° C. was then effected with stirring at about 70 rpm. By applying a vacuum and eliminating the vacuum with nitrogen three times, air was exchanged for nitrogen. After the stirrer speed had been increased to 300 rpm, nitrogen was passed through the mixture from below for 72 minutes with the vacuum pump running and at a pressure of about 0.1 bar. Thereafter, a pressure of 0.3 bar was established by means of nitrogen and 242 g of propylene oxide (PO) were passed in at the start of the polymerisation. The pressure increased to 2.03 bar thereby. After 8 minutes, the pressure had dropped again to 0.5 bar and a further 12.538 kg of PO were metered in over a period of 2 h 11 min at 2.34 bar. 17 minutes after the end of the PO metering, a vacuum was applied at a residual pressure of 1.29 bar and complete devolatilisation was effected. The product was stabilised by addition of 7.5 g of Irganox 1076 and was obtained as a colourless, viscous liquid (OH number: 27.8 mg KOH/g, viscosity at 25° C.: 1165 mPas).

Catalyst Used (Component E))

Fomrez® UL28: urethanisation catalyst, dimethylbis[(1-oxoneodecl)oxy]stannane, commercial product of Momentive Performance Chemicals, Wilton, Conn., USA, used as a 10% strength solution in N-ethylpyrrolidone (component E1)).

Radiation-Curing Groups Used (Component B))

Component B1) Phosphorothioyltris(oxy-4,1-phenylene-iminocarbonyloxyethane-2,1-diyl)triacrylate The refractive index $n_{Mo}$ is 1.579.

Component B2) 2-({[3-(Methylsulphanyl)phenyl]carbamoyl}oxy)ethyl prop-2-enoate.

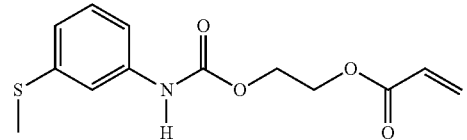

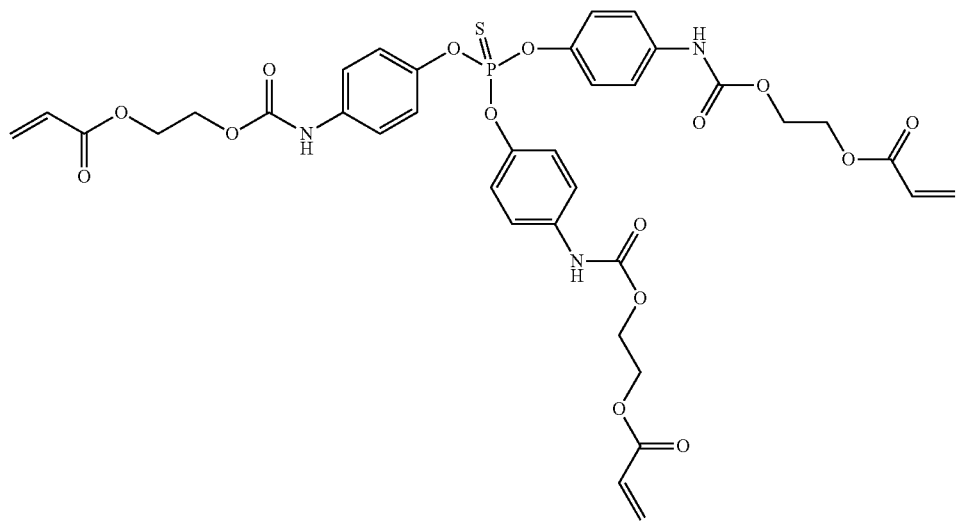 [SMILES: C=CC(=O)OCCOC(=O)Nc1ccc(OP(=S)(Oc2ccc(NC(=O)OCCOC(=O)C=C)cc2)Oc2ccc(NC(=O)OCCOC(=O)C=C)cc2)cc1]

In a 500 ml round-bottomed flask, 0.1 g of 2,6-di-tert-butyl-4-methylphenol, 213.07 g of a 27% strength solution of tris(p-isocyanatophenyl)thiophosphate in ethyl acetate (Desmodur RFE, product of Bayer MaterialScience AG) are initially introduced and heated to 60° C. Thereafter, 42.37 g of 2-hydroxyethyl acrylate are added dropwise and the mixture is further kept at 60° C. until the isocyanate content has fallen below 0.1%. Thereafter, cooling is effected and the ethyl acetate is completely removed in vacuo. The product is obtained as a semicrystalline solid.

In a 100 ml round-bottomed flask, 0.02 g of 2,6-di-tert-butyl-4-methylphenol, 0.01 g of Desmorapid Z, 11.7 g of 3-(methylthio)phenyl isocyanate were initially introduced and initially introduced and heated to 60° C. Thereafter, 8.2 g of 2-hydroxyethyl acrylate were added dropwise and the mixture was further kept at 60° C. until the isocyanate content had fallen below 0.1%. Cooling was then effected. The product was obtained as a colourless liquid.

The refractive index $n_{Mo}$ is 1.576.

Component B3) Sartomer® SR349 ethoxylated (3) bisphenol A diacrylate

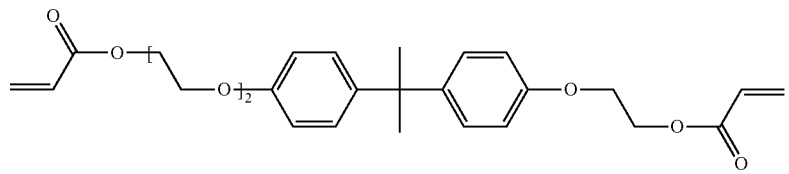

Sartomer® SR349 is a product of Sartomer Company, 502 Thomas Jones Way Exton, Pa. 19341 (USA).

The refractive index $n_D^{20}=n_{Mo}$ is 1.543 (data in manufacturer's data sheet).

Component B4) Mixture of 3-[(2-methylacryloyl)oxy]-2-[(3-methylthiophenylcarbamoyl)oxy]-propyl naphthalene-1-carboxylate

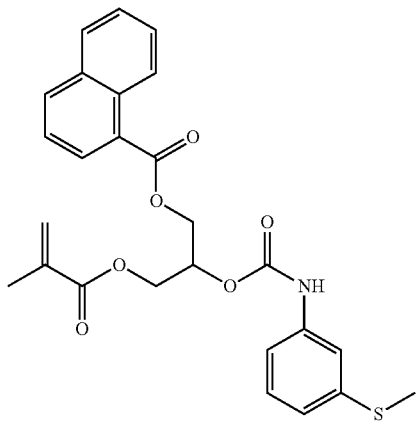 [SMILES: C=C(C)C(=O)OCC(COC(=O)c1cccc2ccccc12)OC(=O)Nc1cccc(SC)c1]

and 2-[(2-methylacryloyl)oxy]-1-{[(3-methylthiophenyl-carbamoyl)oxy]methyl}ethyl naphthalene-1-carboxylate

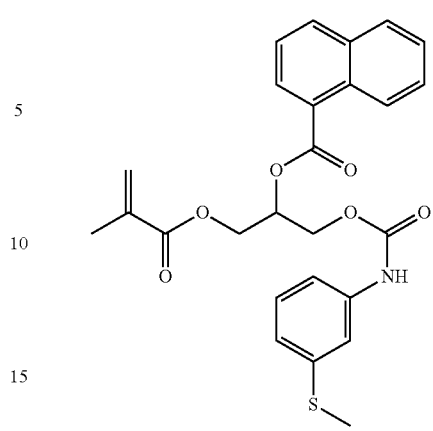

9.4 g of the product from Example 1.1 and 1 mg of dibutyltin dilaurate are initially introduced at 60° C. into a three-necked flask having a stirrer and reflux condenser and air is slowly passed through. 5.0 g of m-methylthiophenyl isocyanate are now added dropwise in the course of 25 minutes under exothermic conditions. Stirring is effected for a further 21 hours, and a clear, yellowish product having an NCO content of 0% is obtained.

The refractive index $n_{Mo}$ is 1.617.

Component B5) {[4-({[(1,1,1,3,3,3-Hexafluoropropan-2-yl)oxy]carbonyl}amino)phenoxy]-phosphorothioyl}bis (oxybenzene-4,1-diylcarbamoyloxyethane-2,1-diyl)bisacrylate

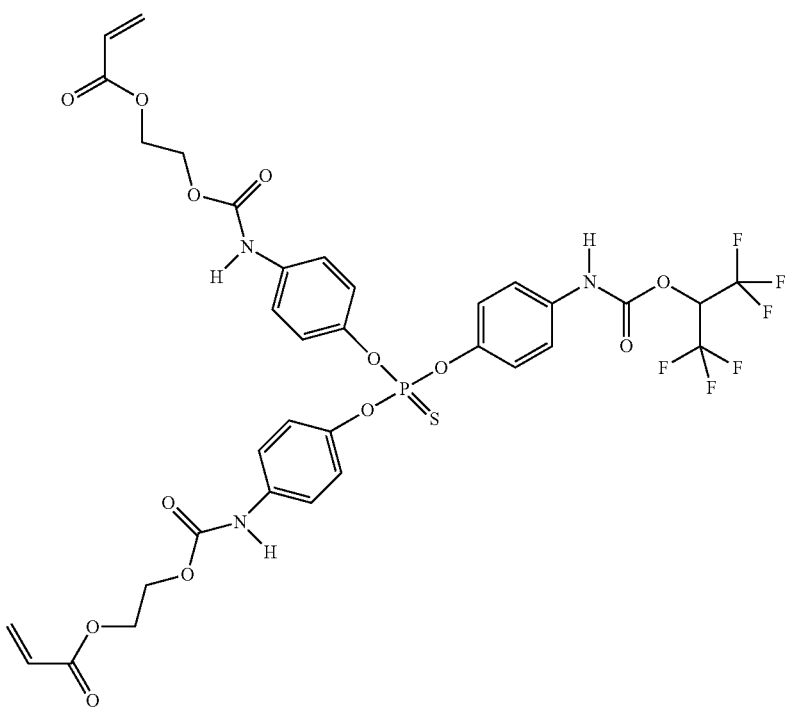 [SMILES: C=CC(=O)OCCOC(=O)Nc1ccc(OP(=S)(Oc2ccc(NC(=O)OCCOC(=O)C=C)cc2)Oc2ccc(NC(=O)OC(C(F)(F)F)C(F)(F)F)cc2)cc1]

In a 2l round-bottomed flask, 0.5 g of 2,6-di-tert-butyl-4-methylphenol, 0.25 g of dibutyltin dilaurate (Desmorapid Z, Bayer MaterialScience AG, Leverkusen, Germany) and and 1.00 kg of a 27% strength solution of tris(p-isocyanatophenyl)thiophosphate in ethyl acetate (Desmodur® RFE, product of Bayer MaterialScience AG, Leverkusen, Germany) were initially introduced and heated to 60° C. Thereafter, 95.3 g of hexafluoroisopropanol were added dropwise and the temperature was maintained for 8 h. Thereafter, 133.5 g of 2-hydroxyethyl acrylate were added dropwise and the mixture was further kept at 60° C. until the isocyanate content had fallen below 0.1%. Thereafter, cooling was effected and the ethyl acetate was completely removed in vacuo. The product was obtained as a colourless oil.

The refractive index $n_{Mo}$ is 1.584.

Component B6) A mixture of (4-methylbenzene-1,3-diyl) bis[carbamoyloxy-3-(biphenyl-2-yloxy)propane-2,1-diyl] bisacrylate and (4-methylbenzene-1,3-diyl)bis[carbamoyloxy-3-(biphenyl-2-yloxy)propane-1,2-diyl]bisacrylate and analogous isomers.

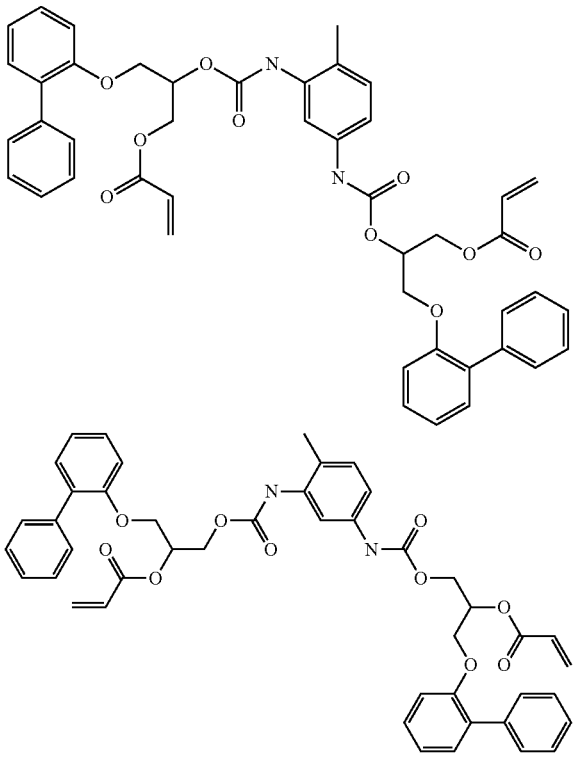

Precursor component B6.1: 430.2 g of Denacol EX 142 (Nagase-Chemtex, Japan), 129.7 g of acrylic acid, 1.18 g of triphenylphosphine and 0.0056 g of 2,6-di-tert-butyl-4-methylphenol were initially introduced into a three-necked flask having a reflux condenser and stirrer. In addition, air was slowly passed through and thermostating was effected at 60° C. Stirring is then effected for 24 hours at 90° C. A clear liquid having an OH number of 157.8 mg KOH/g was obtained.

21.3 g of the precursor from component B6.1 and 5.2 g of a mixture of 2,4- and 2,6-toluidene diisocyanate (Desmodur T80, Bayer MaterialScience AG, Leverkusen, Germany) were initially introduced into a three-necked flask having a reflux condenser and stirrer. In addition, air was slowly passed through and thermostating was effected at 60° C. After an initial exothermic reaction, the product was stirred for 24 hours at 60° C. A clear, colourless, glossy product having an NCO=0% was obtained.

The refractive index $n_{Mo}$ is 1.611.

Photoinitiator Systems Used (Component C))
Description of the System New Methylene Blue+CGI 909 (Component C1))

In a beaker, 0.1 g of new methylene blue, 1.00 g of CGI 909 ((tetrabutylammonium tris(3-chloro-4-methylphenyl) (hexyl)borate, [1147315-11-4]) is an experimental product produced by Ciba Inc., Basle, Switzerland) are dissolved in 3.50 g of N-ethylpyrrolidone in the dark or under suitable illumination. The corresponding percentages by weight of this solution are used for producing the example media.

Description of the System Safranine O+CGI (Component C2))

In a beaker, 0.1 g of safranine O, 1.00 g of CGI 909 ((tetrabutylammonium tris(3-chloro-4-methylphenyl) (hexyl)borate, [1147315-11-4]) is an experimental product produced by Ciba Inc., Basle, Switzerland) are dissolved in 3.50 g of N-ethylpyrrolidone in the dark or under suitable illumination. The corresponding percentages by weight of this solution are used for producing the example media.

Description of the System New Methylene Blue+Safranine O+CGI 909 (Component C3))

Component C3 is a 1:1 mixture of component C1 and component C2. The corresponding percentages by weight of this solution are used for producing the example media.

Description of the UV Initiator TPO (Component C4))

Darocur® TPO (diphenyl(2,4,6-trimethylberizoyl)phosphine oxide) is a product of Ciba Inc., Basle, Switzerland. The corresponding percentages by weight of this product for producing the example media are weighed in in the dark or under suitable illumination.

Non-Photopolymerisable Components Used (Component D))

Description of Component D1) bis(2,2,3,3,4,4,5,5,6,6,7,7-dodecafluoroheptyl)-(2,2,4-trimethylhexane-1,6-diyl)bis-carbamate In a 50 ml round-bottomed flask, 0.02 g of Desmorapid Z and 3.6 g of 2,4,4-trimethylhexane 1,6-diisocyanate (TMDI) were initially introduced and heated to 60° C. Thereafter, 11.9 g of 2,2,3,3,4,4,5,5,6,6,7,7-dodecafluoroheptan-1-ol were added dropwise and the mixture was further kept at 60° C. until the isocyanate content had fallen below 0.1%. Cooling was then effected. The product was obtained as a colourless oil.

The refractive index $n_D^{20}=n_{CA}$ is 1.384.

Description of Component D2) 2,2,3,3,4,4,5,5,6,6,7,7,8,8,9,9-hexadecafluorononyl butylcarbamate In a 1 l round-bottomed flask, 0.50 g of Desmorapid Z and 186 g of n-butyl isocyanate were initially introduced and heated to 60° C. Thereafter, 813 g of 2,2,3,3,4,4,5,5,6,6,7,7,8,8,9,9-hexadecafluorononanol were added dropwise and the mixture was further kept at 60° C. until the isocyanate content had fallen below 0.1%. Cooling was then effected. The product was obtained as a colourless oil.

The refractive index $n_D^{20}=n_{CA}$ is 1.356.

Compositions and Production of the Samples and Example Media:

Production of the Samples for Determining the Refractive Index and the Glass Transition Temperature The following three-dimensionally crosslinked polymers as matrix component A) of the photopolymer formulation for determining the refractive index $n_{Ma}$ were prepared and measured according to the process described above. Likewise, the refractive indices $n_{Mo}$ or $n_{CA}$ of the photopolymerisable monomers components B) or of the non-photopolymerisable components D) were experimentally determined as described above. Table 1 describes the exact compositions and results. NCO:OH designates the equivalent ratio of the functional groups in the components a) and b) in the respective component A).

TABLE 1

| Matrix | Isocyanate component a) | Proportion (g) | Isocyanate-reactive component b) | Proportion (g) | NCO:OH | Catalyst in solution Component E) | Proportion (g) | $n_{Ma}$ | $T_G$ (° C.) |
|---|---|---|---|---|---|---|---|---|---|
| A1 | a1 | 26.6 | b1 | 73.0 | 1.02:1 | E1 | 0.400 | 1.455 | −61 |
| A2 | a2 | 1.68 | b2 | 13.3 | 1.02:1 | E1 | 0.045 | 1.464 | −67 |
| A3 | a3 | 15.4 | b3 | 84.2 | 1.02:1 | E1 | 0.400 | 1.482 | −64 |
| A4 | a2 | 1.72 | b4 | 13.3 | 1.02:1 | E1 | 0.045 | 1.459 | −64 |
| A5 | a4 | 1.47 | b4 | 13.50 | 1.02:1 | E1 | 0.060 | 1.460 | −64 |

| Component B | $n_{Mo}$ | $T_G$ (° C.) |
|---|---|---|
| B1 | 1.576 | 20 |
| B2 | 1.579 | −21 |
| B3 | 1.543 | −32 |
| B4 | 1.617 | 12 |
| B5 | 1.584 | −16 |
| B6 | 1.611 | 26 |

| Component D | $n_{C4}$ | $T_G$ (° C.) |
|---|---|---|
| D1 | 1.384 | |
| D2 | 1.356 | |

Preparation of the Photopolymer Formulation with UV Initiator for Determining the Modulus $G_0$ and $G_{UV}$ of the Photopolymers Before and After the UV Crosslinking.

For the preparation of the photopolymer formulation for determining the modulus $G_{UV}$ of the photopolymers after UV crosslinking, component B), component C4) (which may already have been dissolved beforehand in component B)) and optionally additives are dissolved in the isocyanate-reactive component b), optionally at 60° C. Optionally, heating is effected for not more than 10 minutes in a drying oven at 60° C. Thereafter, isocyanate component a) is added and mixing is effected in a Speedmixer for 1 minute. Subsequently, a solution of component E1) in butyl acetate is added and mixing is effected again in a Speedmixer for 1 minute. The concentration of component E1) in butyl acetate is 10 percent by weight. The amounts of this solution which are described in Table 2 were used.

Table 2 lists the investigated examples of the photopolymer formulations for determining the modulus $G_{UV}$ of the photopolymers after UV crosslinking, which do not have an exclusive character in their composition. These photopolymer formulations were prepared according to the method which was described in the section on the determination of the modulus $G_{UV}$ of the photopolymers after UV crosslinking by means of an oscillation rheometer.

TABLE 2

| Photopolymer formulation with UV initiator (F) | Isocyanate component a) | Proportion (g) | Isocyanate-reactive component b) | Proportion (g) | NCO:OH | Photo-polymerisable monomer 1 (component B)) | Proportion (% by weight) | Photo-polymerisable monomer 2 (component B)) |
|---|---|---|---|---|---|---|---|---|
| F I | a1 | 1.853 | b1 | 5.137 | 1.02:1 | B1 | X | B2 |
| F II | a2 | 0.534 | b2 | 3.950 | 1.02:1 | B1 | X | B2 |
| F III | a2 | 0.534 | b2 | 3.950 | 1.02:1 | B1 | X | B2 |
| F IV | a3 | 0.707 | b3 | 3.783 | 1.02:1 | B1 | X | B2 |
| F V | a3 | 0.707 | b3 | 3.783 | 1.02:1 | B1 | X | B2 |
| F VI | a3 | 0.936 | b3 | 5.054 | 1.02:1 | B1 | X | B4 |
| F VII | a2 | 0.534 | b2 | 3.950 | 1.02:1 | B1 | X | B2 |
| F VIII | a2 | 0.534 | b2 | 3.950 | 1.02:1 | B1 | X | B2 |
| F IX | a3 | 0.707 | b3 | 3.783 | 1.02:1 | B5 | X | B2 |
| F X | a3 | 0.707 | b3 | 3.783 | 1.02:1 | B1 | X | B2 |
| F XI | a3 | 0.707 | b3 | 3.783 | 1.02:1 | B1 | X | B2 |
| F XII | a2 | 0.661 | b4 | 5.326 | 1.02:1 | B1 | X | B2 |
| F XIII | a2 | 0.534 | b2 | 3.950 | 1.02:1 | B5 | X | B2 |
| F XIV | a2 | 0.534 | b2 | 3.950 | 1.02:1 | B6 | X | B2 |
| F A | a4 | 0.573 | b4 | 5.414 | 1.02:1 | B1 | X | B3 |
| F B | a2 | 0.534 | b2 | 3.950 | 1.02:1 | B1 | X | B6 |
| F C | a2 | 0.534 | b2 | 3.950 | 1.02:1 | B1 | X | B5 |
| F D | a3 | 0.707 | b3 | 3.783 | 1.02:1 | B1 | X | B5 |

| Photopolymer formulation with UV initiator (F) | Proportion (% by weight) | Non-photo-polymerisable component D | Proportion (% by weight) | UV initiator (component C)) | Proportion (g) | Catalyst in solution (butyl acetate) (component E)) | Proportion (g) |
|---|---|---|---|---|---|---|---|
| F I | 30.0 − X | | | C4 | 0 | E1 | 0.0280 |
| F II | 30.0 − X | D1 | 25.0 | C4 | 0 | E1 | 0.0350 |
| F III | 40.0 − X | D1 | 15.0 | C4 | 0 | E1 | 0.0350 |
| F IV | 30.0 − X | D2 | 25.0 | C4 | 0 | E1 | 0.0138 |
| F V | 40.0 − X | D2 | 15.0 | C4 | 0 | E1 | 0.0138 |
| F VI | 40.0 − X | | | C4 | 0 | E1 | 0.0095 |

TABLE 2-continued

| | | | | | | | |
|---|---|---|---|---|---|---|---|
| F VII | 30.0 − X | D2 | 25.0 | C4 | 0 | E1 | 0.0350 |
| F VIII | 40.0 − X | D2 | 15.0 | C4 | 0 | E1 | 0.0350 |
| F IX | 40.0 − X | D2 | 15.0 | C4 | 0 | E1 | 0.0138 |
| F X | 30.0 − X | D1 | 25.0 | C4 | 0 | E1 | 0.0138 |
| F XI | 40.0 − X | D1 | 15.0 | C4 | 0 | E1 | 0.0138 |
| F XII | 40.0 − X | | | C4 | 0 | E1 | 0.0587 |
| F XIII | 30.0 − X | D1 | 25.0 | C4 | 0 | E1 | 0.0350 |
| F XIV | 30.0 − X | D1 | 25.0 | C4 | 0 | E1 | 0.0350 |
| F A | 40.0 − X | | | C4 | 0 | E1 | 0.0295 |
| F B | 30.0 − X | D1 | 25.0 | C4 | 0 | E1 | 0.0350 |
| F C | 30.0 − X | D1 | 25.0 | C4 | 0 | E1 | 0.0350 |
| F D | 40.0 − X | D2 | 15.0 | C4 | 0 | E1 | 0.0138 |

Production of the Holographic Media Based on Photopolymer Formulation with Photoinitiator for Determining the Refractive Index Contrast Δn.

Holographic media (cf. Table 3) in which the photopolymer is present as a layer between glass sheets of 1 mm thickness each were produced from the photopolymer formulations. This type of holographic media is particularly suitable for determining the performance thereof according to the methods described in the section "Measurement of the holographic properties DE and Δn of the holographic media by means of two-beam interference in reflection arrangement" and is therefore not meant to be limiting in the context of the formulated claims to the holographic media, provided that the photopolymer formulation used complies with the claimed properties with regard to modulus $G_{UV}$ of the photopolymers after UV crosslinking and the maximum variation of Δn.

Exemplary Production of the Holographic Media

For the production of the holographic media, component B), component C) (which may already be predissolved in component B)) and optionally the additives are dissolved in the isocyanate-reactive component b) in the dark, optionally at 60° C., glass beads having a size of 20 μm or 10 μm (e.g. from Whitehouse Scientific Ltd, Waverton, Chester, CH3 7PB, United Kingdom) are then added and thorough mixing is effected (Speedmixer). Optionally, heating is effected for not more than 10 minutes in a drying oven at 60° C. Thereafter, the isocyanate component a) is added and mixing is effected again in a Speedmixer for 1 minute. Subsequently, a solution of component E1) is added and mixing is effected again in a Speedmixer for 1 minute. The mixture obtained is devolatilised with stirring at <1 mbar for not more than 30 seconds, after which it is distributed over glass plates measuring 50×75 mm and these are each covered with a further glass plate. The curing of the PU formulation is effected under 15 kg weights over several hours (usually overnight). In some cases, the media are postcured in light-tight packaging for a further 2 hours at 60° C. Since different formulations with different starting viscosity and different curing rate of the matrix do not always lead to the same layer thicknesses d' of the photopolymer layer, d' is determined separately on the basis of the characteristics of the recorded holograms for each sample.

TABLE 3

| Holographic medium (M) | Isocyanate component a) | Proportion (g) | Isocyanate-reactive component b) | Proportion (g) | NCO:OH | Photo-polymerisable monomer 1 (component B)) | Proportion (% by weight) | Photo-polymerisable monomer 2 (component B)) |
|---|---|---|---|---|---|---|---|---|
| M I | a1 | 2.604 | b1 | 7.192 | 1.02:1 | B1 | X | B2 |
| M II | a2 | 0.479 | b2 | 3.544 | 1.02:1 | B1 | X | B2 |
| M III | a2 | 0.479 | b2 | 3.544 | 1.02:1 | B1 | X | B2 |
| M IV | a3 | 0.623 | b3 | 3.401 | 1.02:1 | B1 | X | B2 |
| M V | a3 | 0.623 | b3 | 3.401 | 1.02:1 | B1 | X | B2 |
| M VI | a3 | 0.854 | b3 | 4.669 | 1.02:1 | B1 | X | B4 |
| M VII | a2 | 0.479 | b2 | 3.544 | 1.02:1 | B1 | X | B2 |
| M VIII | a2 | 0.479 | b2 | 3.544 | 1.02:1 | B1 | X | B2 |
| M IX | a3 | 0.630 | b3 | 3.404 | 1.02:1 | B5 | X | B2 |
| M X | a3 | 0.644 | b3 | 3.379 | 1.02:1 | B1 | X | B2 |
| M XI | a3 | 0.644 | b3 | 3.379 | 1.02:1 | B1 | X | B2 |
| M XII | a2 | 0.633 | b4 | 4.890 | 1.02:1 | B1 | X | B2 |
| M XIII | a2 | 0.479 | b2 | 3.544 | 1.02:1 | B5 | X | B2 |
| M XIV | a2 | 0.479 | b2 | 3.544 | 1.02:1 | B6 | X | B2 |
| M A | a4 | 0.553 | b4 | 4.970 | 1.02:1 | B1 | X | B3 |
| M B | a2 | 0.479 | b2 | 3.544 | 1.02:1 | B1 | X | B6 |
| M C | a2 | 0.479 | b2 | 3.544 | 1.02:1 | B1 | X | B5 |

| Holographic medium (M) | Proportion (% by weight) | Non-photo-polymerisable component D | Proportion (% by weight) | Photo-initiator (component C)) | Proportion (g) | Catalyst in solution (component E)) | Proportion (g) | Corresponds to formulation with UV initiator (F) |
|---|---|---|---|---|---|---|---|---|
| M I | 30.0 − X | | | C3 | 0.690 | E1 | 0.029 | F I |
| M II | 30.0 − X | D1 | 25.0 | C1 | 0.442 | E1 | 0.020 | F II |
| M III | 40.0 − X | D1 | 15.0 | C1 | 0.442 | E1 | 0.020 | F III |
| M IV | 30.0 − X | D2 | 25.0 | C1 | 0.441 | E1 | 0.020 | F IV |
| M V | 40.0 − X | D2 | 15.0 | C1 | 0.441 | E1 | 0.020 | F V |
| M VI | 40.0 − X | | | C1 | 0.442 | E1 | 0.020 | F VI |
| M VII | 30.0 − X | D2 | 25.0 | C1 | 0.442 | E1 | 0.020 | F VII |
| M VIII | 40.0 − X | D2 | 15.0 | C1 | 0.442 | E1 | 0.020 | F VIII |

TABLE 3-continued

| | | | | | | | | |
|---|---|---|---|---|---|---|---|---|
| M IX | 40.0 – X | D2 | 15.0 | C1 | 0.445 | E1 | 0.006 | F IX |
| M X | 30.0 – X | D1 | 25.0 | C1 | 0.442 | E1 | 0.020 | F X |
| M XI | 40.0 – X | D1 | 15.0 | C1 | 0.442 | E1 | 0.020 | F XI |
| M XII | 40.0 – X | | | C2 | 0.442 | E1 | 0.020 | F XII |
| M XIII | 30.0 – X | D1 | 25.0 | C1 | 0.442 | E1 | 0.020 | F XIII |
| M XIV | 30.0 – X | D1 | 25.0 | C1 | 0.442 | E1 | 0.020 | F XIV |
| M A | 40.0 – X | | | C2 | 0.422 | E1 | 0.020 | F A |
| M B | 30.0 – X | D1 | 25.0 | C1 | 0.422 | E1 | 0.020 | F B |
| M C | 30.0 – X | D1 | 25.0 | C1 | 0.422 | E1 | 0.020 | F C |

Results from $G_{UV}$ and Variation of $\Delta n$ Combined.

The following measured values for $G_0$ (MPa), $G_{UV}$ (MPa), $\Delta n$ and variation of $\Delta n$ (%) at the dose E (mJ/cm$^2$) were obtained and are shown in Table 4a and 4b. The $\Delta n$ values marked with * were measured at $\lambda$=532 nm instead of at $\lambda$=633 nm.

TABLE 4a

Figure 4:
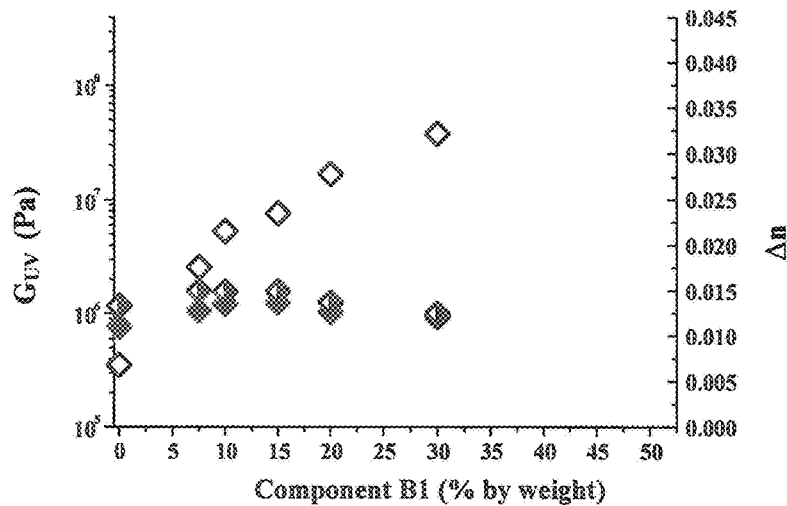
FIG. 4 illustrates a graph showing holographic property test results obtained from an example according to an embodiment of the present invention.
Figure 5:
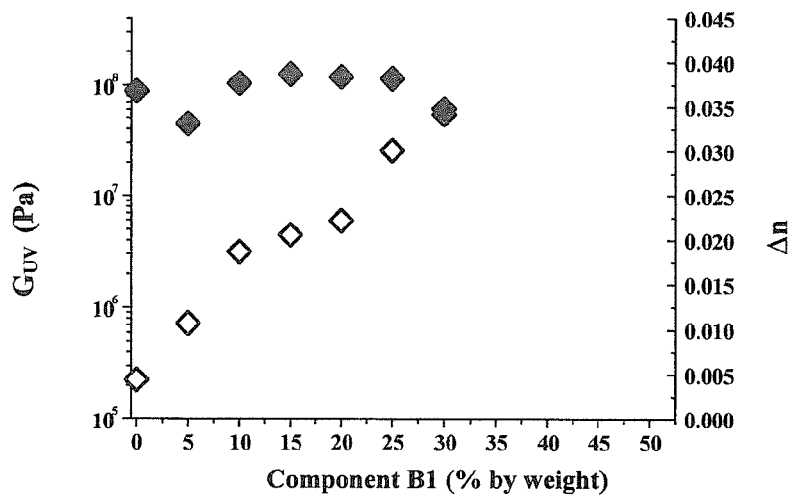
FIG. 5 illustrates a graph showing holographic property test results obtained from an example according to an embodiment of the present invention.
Figure 6:
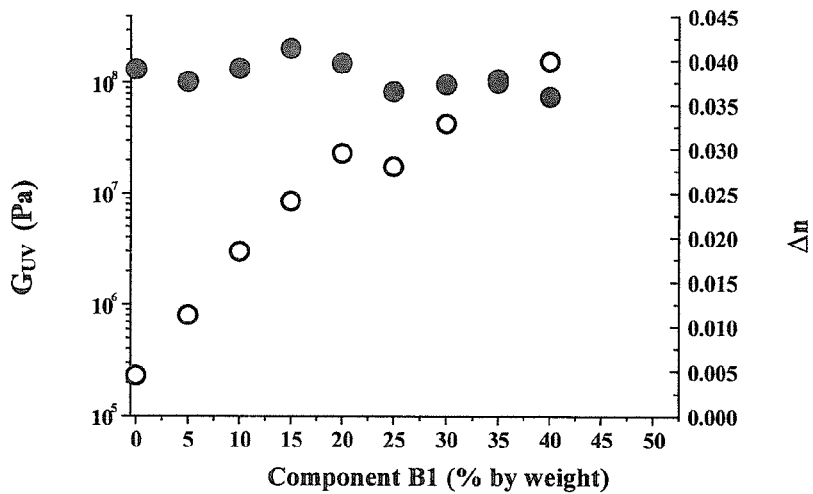
FIG. 6 illustrates a graph showing holographic property test results obtained from an example according to an embodiment of the present invention.
Figure 7:
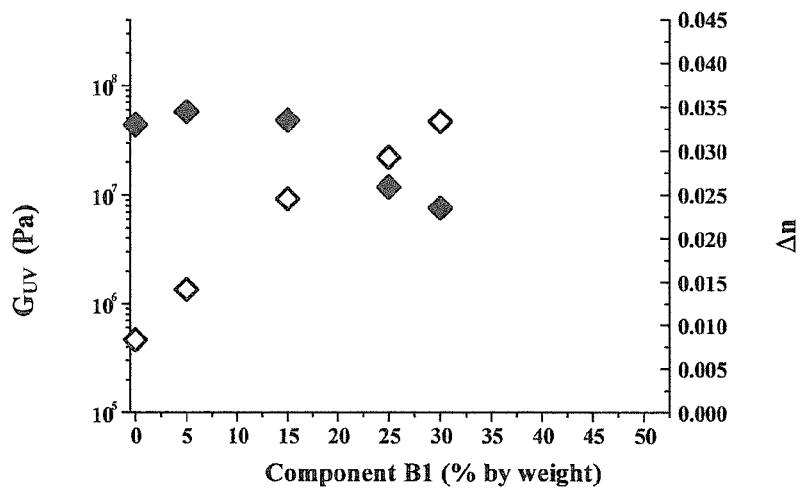
FIG. 7 illustrates a graph showing holographic property test results obtained from an example according to an embodiment of the present invention.
Figure 8:
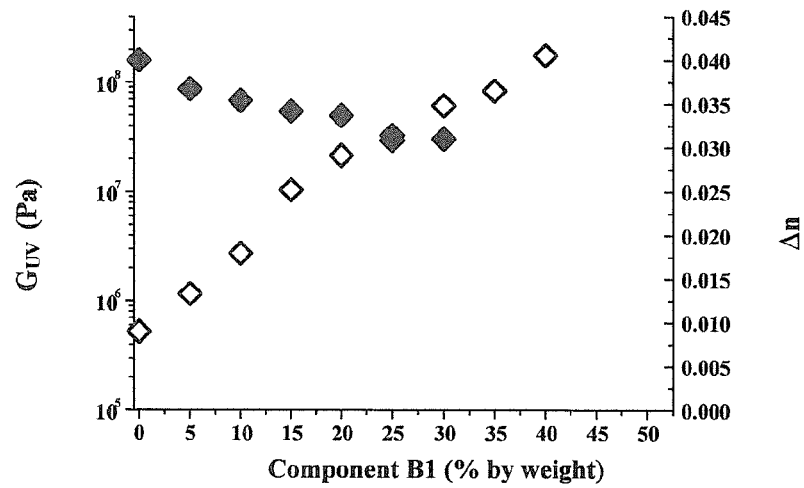
FIG. 8 illustrates a graph showing holographic property test results obtained from an example according to an embodiment of the present invention.
Figure 9:
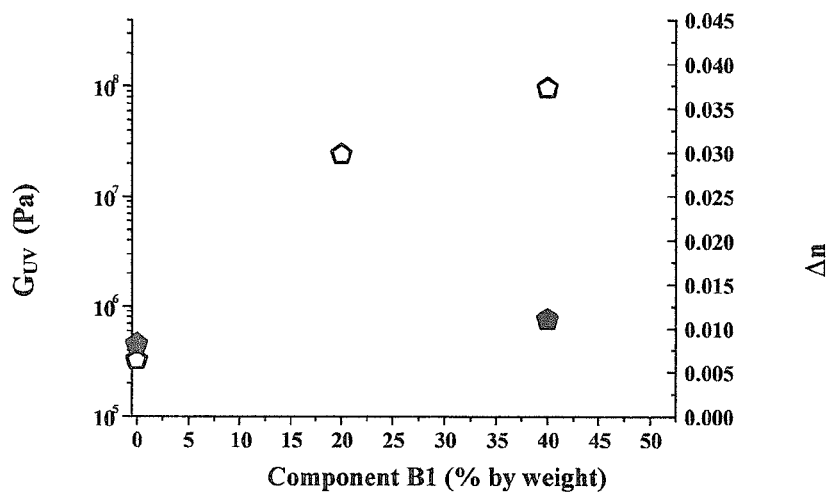
FIG. 9 illustrates a graph showing holographic property test results obtained from an example according to an embodiment of the present invention.
Figure 10:
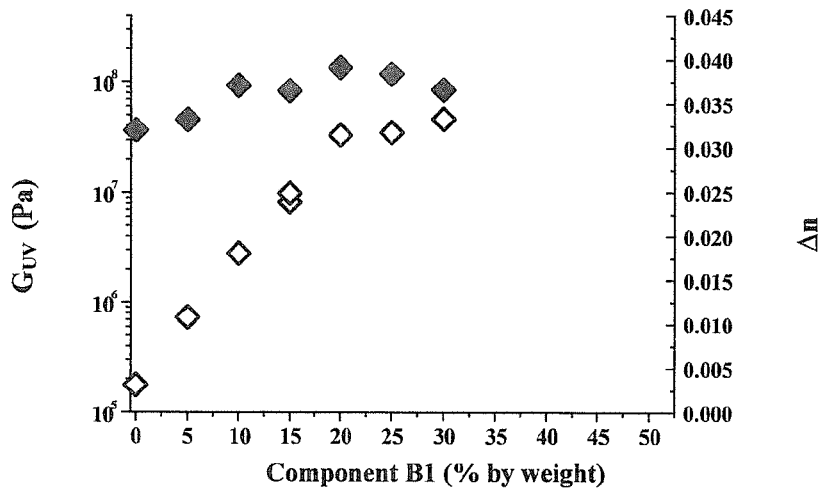
FIG. 10 illustrates a graph showing holographic property test results obtained from an example according to an embodiment of the present invention.
Figure 11:
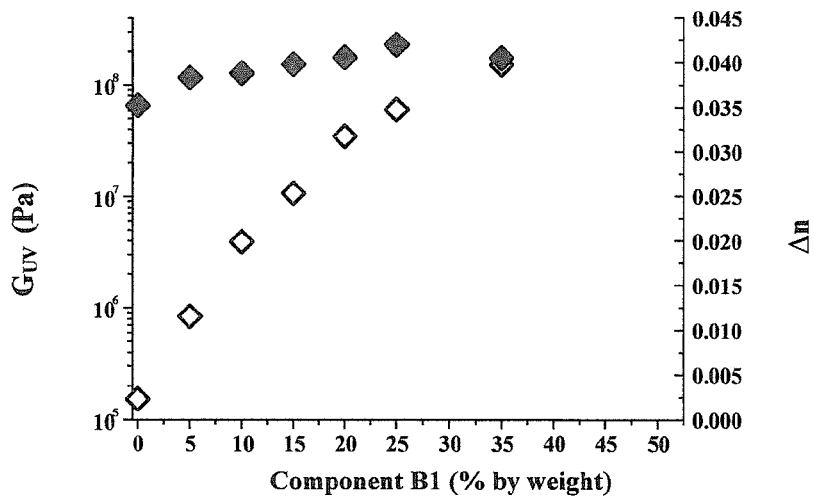
FIG. 11 illustrates a graph showing holographic property test results obtained from an example according to an embodiment of the present invention.
Figure 12:
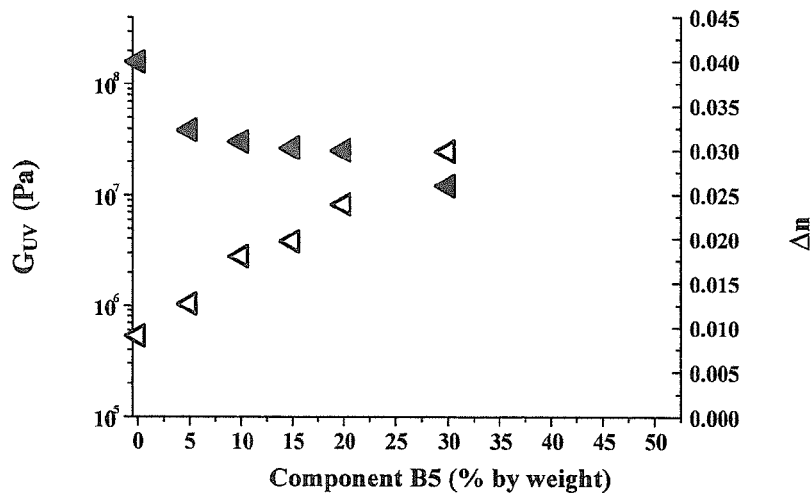
FIG. 12 illustrates a graph showing holographic property test results obtained from an example according to an embodiment of the present invention.
Figure 13:
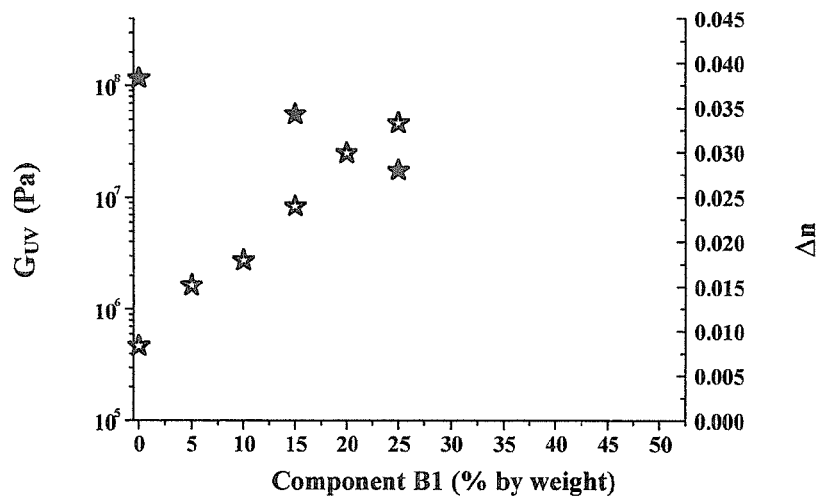
FIG. 13 illustrates a graph showing holographic property test results obtained from an example according to an embodiment of the present invention.
Figure 14:
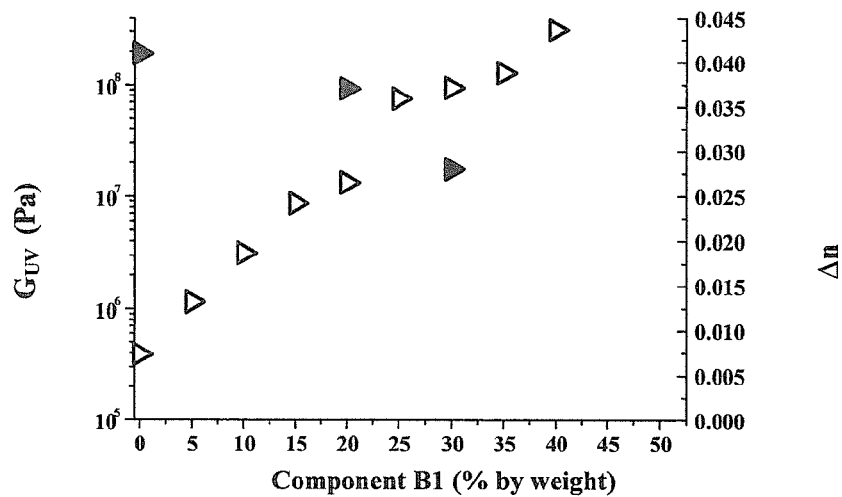
FIG. 14 illustrates a graph showing holographic property test results obtained from an example according to an embodiment of the present invention.
Figure 15:
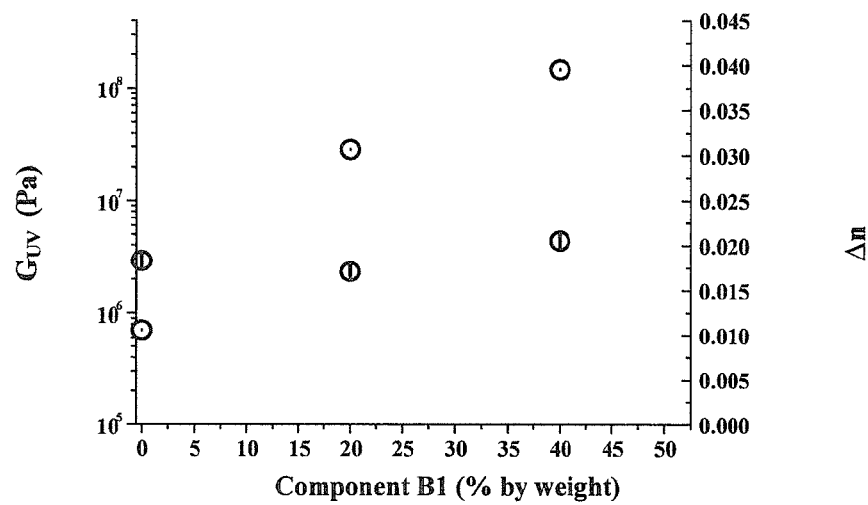
FIG. 15 illustrates a graph showing holographic property test results obtained from an example according to an embodiment of the present invention.
Figure 16:
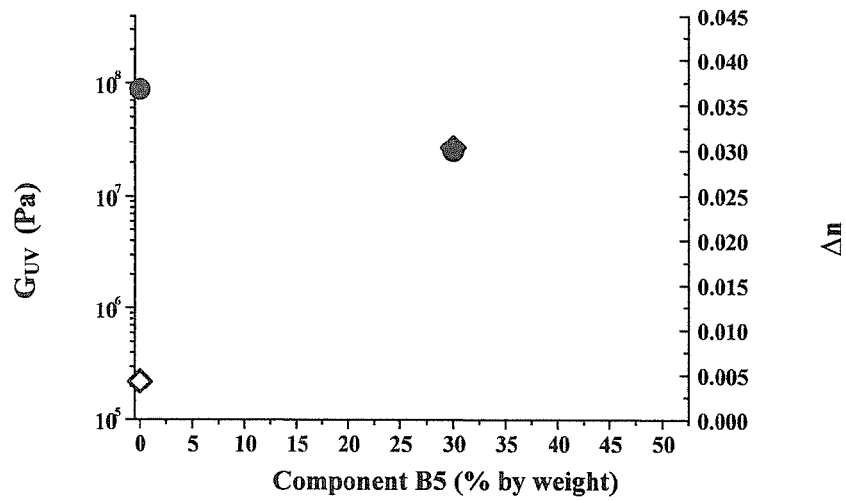
FIG. 16 illustrates a graph showing holographic property test results obtained from an example according to an embodiment of the present invention.
Figure 17:
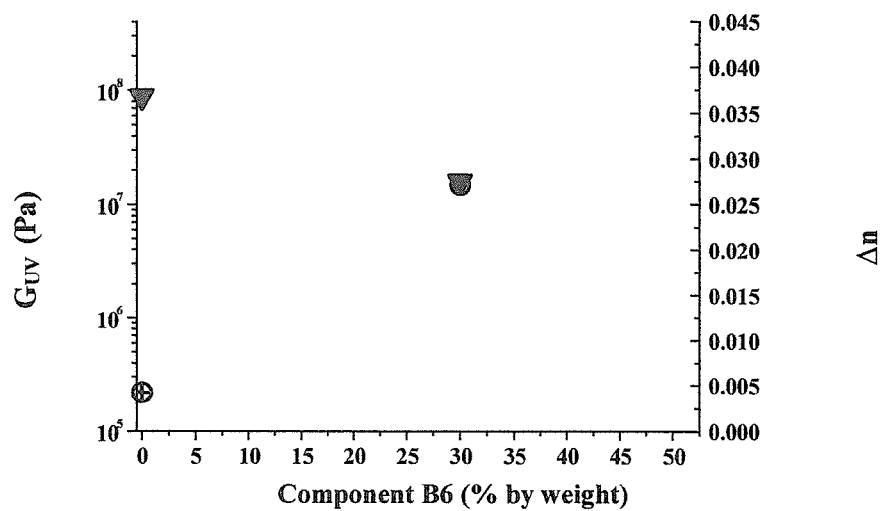
FIG. 17 illustrates a graph showing holographic property test results obtained from an example according to an embodiment of the present invention.
Figure 18:
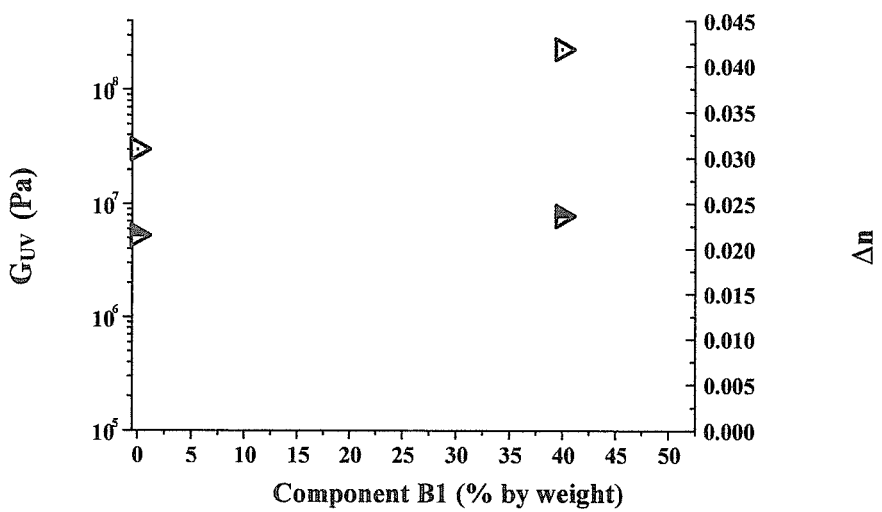
FIG. 18 illustrates a graph showing holographic property test results obtained from a comparative example.
Figure 19:
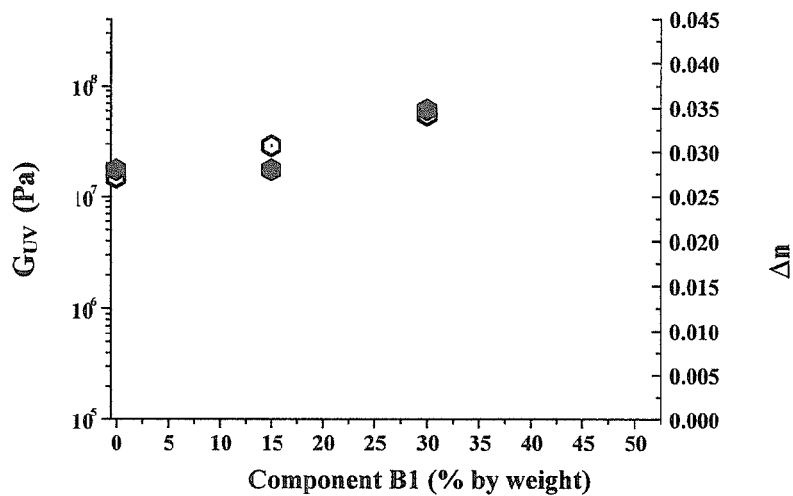
FIG. 19 illustrates a graph showing holographic property test results obtained from a comparative example.
Figure 20:
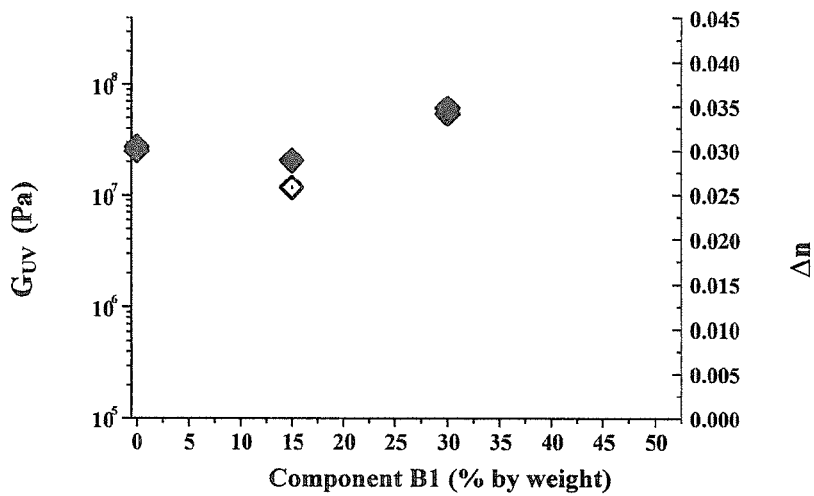
FIG. 20 illustrates a graph showing holographic property test results obtained from a comparative example.
Figure 21:
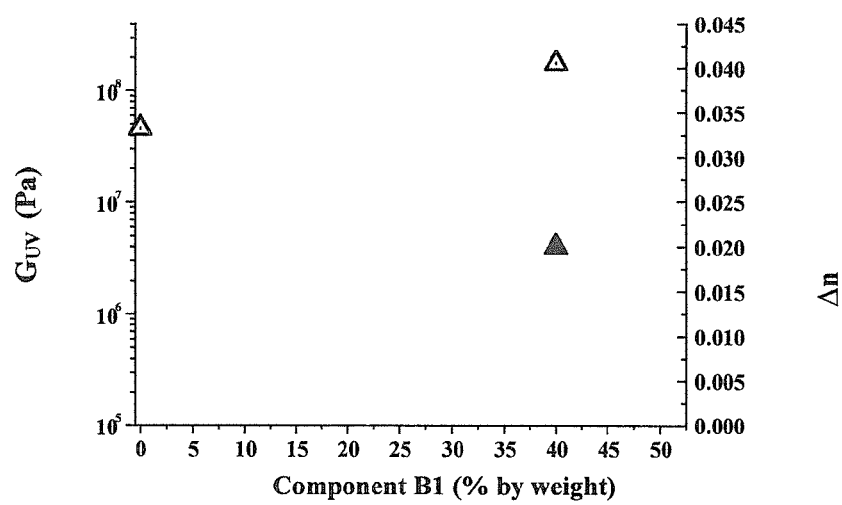
FIG. 21 illustrates a graph showing holographic property test results obtained from a comparative example.

| Example type | Holographic medium (M) | $\Delta n$ | Variation of $\Delta n$ | Corresponds to formulation with UV initiator (F) | Total proportion of components b) in the photopolymer (%) | $G_0$ |
|---|---|---|---|---|---|---|
| Example 1 according to the invention; FIG. 4 | M I | 0.011-0.012 | 9 | F I | 30 | 0.09-0.19 |
| Example 1 according to the invention; FIG. 4 | M I | 0.013*-0.015* | 15 | F I | 30 | 0.09-0.19 |
| Example 2 according to the invention; FIG. 5 | M II | 0.033-0.039 | 18 | F II | 30 | 0.06-0.11 |
| Example 3 according to the invention 3; FIG. 6 | M III | 0.036-0.041 | 14 | F III | 40 | 0.05-0.09 |
| Example 4 according to the invention; FIG. 7 | M IV | 0.024-0.035 | 46 | F IV | 30 | 0.32-0.57 |
| Example 5 according to the invention; FIG. 8 | M V | 0.031-0.040 | 29 | F V | 40 | 0.31-0.41 |
| Example 6 according to the invention; FIG. 9 | M VI | 0.008-0.011 | 38 | F VI | 40 | 0.10-0.59 |
| Example 7 according to the invention; FIG. 10 | M VII | 0.032-0.039 | 22 | F VII | 30 | 0.08-0.15 |
| Example 8 according to the invention; FIG. 11 | M VIII | 0.035-0.042 | 17 | F VIII | 40 | 0.04-0.11 |
| Example 9 according to the invention; FIG. 12 | M IX | 0.026-0.040 | 54 | F IX | 40 | 0.29-0.44 |
| Example 10 according to the invention; FIG. 13 | M X | 0.028-0.038 | 37 | F X | 30 | 0.27-0.62 |
| Example 11 according to the invention; FIG. 14 | M XI | 0.028-0.041 | 46 | F XI | 40 | 0.20-0.54 |
| Example 12 according to the invention; FIG. 15 | M XII | 0.017*-0.021* | 24 | F XII | 40 | 0.03-0.08 |
| Example 13 according to the invention; FIG. 16 | M XIII | 0.030-0.037 | 23 | F XIII | 30 | 0.05-0.09 |
| Example 14 according to the invention; FIG. 17 | M XIV | 0.028-0.037 | 32 | F XIV | 30 | 0.01-0.09 |

| Example type | $G_{UV}$ | E | $n_{Ma} - n_{CA}$ | $n_{Mo} - n_{Ma}$ | $T_G$ of component A) |
|---|---|---|---|---|---|
| Example 1 according to the invention; FIG. 4 | 0.35-38 | 4-36 | >+0.121 | | −61 |
| Example 1 according to the invention; FIG. 4 | 0.35-38 | 16-128 | >+0.121 | | −61 |

TABLE 4a-continued

| Example type | $G_{UV}$ | E | $n_{Ma} - n_{CA}$ | $n_{Mo} - n_{Ma}$ | $T_G$ of component A) |
|---|---|---|---|---|---|
| Example 2 according to the invention; FIG. 5 | 0.22-55 | 4-36 | >+0.112 | 0.080 | -67 |
| Example 3 according to the invention 3; FIG. 6 | 0.23-157 | 4-36 | >+0.112 | 0.080 | -67 |
| Example 4 according to the invention; FIG. 7 | 0.47-47 | 4-36 | >+0.094 | 0.126 | -64 |
| Example 5 according to the invention; FIG. 8 | 0.53-61 | 4-36 | >+0.094 | 0.126 | -64 |
| Example 6 according to the invention; FIG. 9 | 0.32-96 | 4-36 | >+0.094 | | -64 |
| Example 7 according to the invention; FIG. 10 | 0.18-46 | 4-36 | >+0.112 | 0.108 | -67 |
| Example 8 according to the invention; FIG. 11 | 0.15-54 | 4-36 | >+0.112 | 0.108 | -67 |
| Example 9 according to the invention; FIG. 12 | 0.53-25 | 4-36 | >+0.102 | 0.126 | -64 |
| Example 10 according to the invention; FIG. 13 | 0.47-46 | 4-36 | >+0.094 | 0.098 | -64 |
| Example 11 according to the invention; FIG. 14 | 0.39-94 | 4-36 | >+0.094 | 0.098 | -64 |
| Example 12 according to the invention; FIG. 15 | 0.70-147 | 4-36 | >+0.094 | | -64 |
| Example 13 according to the invention; FIG. 16 | 0.22-27 | 4-36 | >+0.120 | 0.080 | -67 |
| Example 14 according to the invention; FIG. 17 | 0.22-15 | 4-36 | >+0.120 | 0.080 | -67 |

TABLE 4b

| Example type | Holographic Medium (M) | Δn | Variation of Δn | Corresponds to formulation with UV initiator (F) | Total proportion of components B) in the photopolymer (%) | $G_0$ |
|---|---|---|---|---|---|---|
| Comparative example: A; FIG. A | M A | 0.022*-0.024* | 9 | F A | 40.0 | 0.01-0.02 |
| Comparative example: B; FIG. B | M B | 0.028-0.035 | 25 | F B | 30.0 | 0.01-0.09 |
| Comparative example: C; FIG. C | M C | 0.029-0.035 | 21 | F C | 30.0 | 0.05-0.09 |
| Comparative example: D; FIG. D | M D | n.g. | n.g. | F D | 40.0 | 0.31-0.40 |

| Example type | $G_{UV}$ | E | $n_{Ma} - n_{CA}$ | $n_{Mo} - n_{Ma}$ | $T_G$ of component A) |
|---|---|---|---|---|---|
| Comparative example: A; FIG. A | 30-223 | 8-64 | >+0.083 | | -64 |
| Comparative example: B; FIG. B | 15-55 | 4-32 | >+0.147 | 0.080 | -67 |
| Comparative example: C; FIG. C | 12-55 | 4-32 | >+0.120 | 0.080 | -67 |
| Comparative example: D; FIG. D | 46-176 | 4-32 | >+0.098 | 0.126 | -64 |

The values found for the variation of Δn of the holographic media and for the modulus $G_{UV}$ of the photopolymer formulations after UV crosslinking on variation of the relative content of polyfunctional monomer in a mixture with a monofunctional monomer (components B)) impressively show how the mechanical properties of the photopolymers after UV exposure can be adjusted from flexible and rubber-like consistency to high mechanical hardness without significantly influencing the holographic performance Δn. In mixtures of only polyfunctional writing monomers, no flexible settings of the mechanical modulus can be realised.

The results found are illustrated once again in the following figures, FIG. 4 to FIG. 19 and Figure A to Figure D. These figures show the variation of $G_{UV}$ (open symbols, left y axis) for the formulations with the UV initiator F, Δn (holograms recorded at λ=633 nm, closed symbols, right y axis) and/or Δn (holograms recorded at λ=532 nm, half-open symbols, right y axis) for the media M having the proportion of the photopolymerisable polyfunctional component B, based on the total formulation. The total proportion of the polyfunctional component B and of the monofunctional component B, based on the total formulation, is shown in Tables 4a and 4b.

The invention claimed is:

1. A process for the production of exposed, holographic media comprising a photopolymer formulation having a modulus $G_{UV}$ of between 0.1 to 160 MPa and a Δn≥0.008, wherein the process comprises:
  i) providing a photopolymer formulation comprising:
    A) matrix polymers as an amorphous network,
    B) a combination of a monofunctional writing monomer and a polyfunctional writing monomer,
    C) a photoinitiator system,
    D) optionally a non-photopolymerisable component, and
    E) optionally catalysts, free radical stabilisers, solvents, additives and other auxiliaries and/or additives is provided;
  ii) forming a media which comprises the photopolymer formulation;
  iii) subjecting the media to a holographic exposure procedure in order to record the hologram; and
  iv) exposing the medium as a whole to UV radiation for at least 15 min in order to fix the hologram, and wherein, while exposing the medium to UV, the modulus $G_{UV}$ of the exposed photopolymer formulation is determined by measuring the curing of the matrix in an oscillation rheometer as follows:
    oscillation measuring mode at a constant angular frequency $\omega_0$ of 62.8 rad/s and a controlled logarithmic deformation amplitude ramp deformation amplitude of 0.01%-0.001%
    temperature 50° C., normal force regulation set at 0 Newton
    recording of the storage modulus G' during the UV exposure over the measuring time for at least 15 minutes or until a constant value of G' was reached; this value is taken as $G_{UV}$,
  wherein the writing monomers comprise acrylate- and/or methacrylate-functionalised compounds,
  wherein the total content of writing monomers in the photopolymer formulation is from 30% to 45% by weight,
  wherein the unexposed photopolymer formulation has a modulus $G_0$ of <0.7 MPa, wherein the modulus $G_0$ is determined by measuring the curing of the matrix in an oscillation rheometer as follows:
    plate spacing 250 μm, plate diameter 12 mm
    oscillation measuring mode at a constant angular frequency $\omega_0$ of 62.8 rad/s and a controlled logarithmic deformation amplitude ramp of 10%-0.01%
    temperature 50° C., normal force regulation set at 0 Newton
    recording of the storage modulus G' over the measuring time for at least 2 hours or until a constant value of G' was reached; this value is referred to as $G_0$,
  and the modulus $G_{UV}$ of the exposed photopolymer formulation is adjusted in the intended range of between 0.1 and 160 MPa via the ratio of the relative proportion of the monofunctional writing monomer to the relative proportion of the polyfunctional writing monomer, based on the total writing monomer content, in such a way that a high modulus is realised by a high relative proportion of the polyfunctional writing monomer and a low modulus by a high relative proportion of the monofunctional writing monomer, based on the total writing monomer content, and wherein the Δn of individual exposed, holographic media having different proportions of monofunctional and polyfunctional writing monomers varies by less than 55%, the variation being calculated as follows: $(\Delta n_{max} - \Delta n_{min})/\Delta n_{min} \cdot 100\%$.

2. The process according to claim 1, wherein the exposed, holographic media has a modulus $G_{UV}$ of between 0.3 and 40.

3. The process according to claim 1, wherein the writing monomers and the matrix polymers are chosen so that the refractive index of each of the two writing monomers is either at least 0.05 units greater than the refractive index of the matrix polymers or the refractive index of each of the two writing monomers is at least 0.05 units less than the refractive index of the matrix polymers.

4. The process according to claim 1, wherein the matrix polymers comprise polyurethanes.

5. The process according to claim 4, wherein the polyurethanes are obtained by reacting a component carrying NCO groups and an NCO-reactive component, wherein at least one of the two components have an equivalent weight of more than 200 g/mol.

6. The process according to claim 5, wherein at least one of the two components have an equivalent weight of more than 350 g/mol and wherein no cyclic structures occur in the polymer backbone of the polyurethane.

7. The process according to claim 4, wherein the polyurethanes in the reacted state have a glass transition temperature $T_G$ of <−45° C.

8. The process according to claim 1, wherein the monofunctional writing monomer has the formula (II)

(II)

wherein
$R^1$, $R^2$ independently of one another, represent hydrogen or linear, branched, cyclic or heterocyclic organic radicals which are unsubstituted or optionally also substituted by heteroatoms.

9. The process according to claim 8, wherein the monofunctional writing monomer has a glass transition temperature $T_G$ of <15° C.

10. The process according to claim 1, wherein the polyfunctional writing monomer has a refractive index of $n_D^{20} > 1.50$.

11. The process according to claim 1, wherein the photopolymer formulation further comprises a plasticizer.

12. The process according to claim 11, wherein the plasticizer is chosen so that the refractive index of the plasticizer is at least 0.05 units less than the refractive index of the matrix polymers if both writing monomers have higher refractive indices than the matrix polymers, and the refractive index of the plasticizer is at least 0.05 units greater than the refractive index of the matrix polymers if both writing monomers have refractive indices less than the refractive index of the matrix polymers.

13. The process according to claim 11, wherein the plasticizer comprises a urethane of the formula (VI)

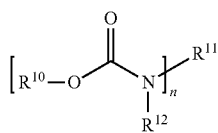

(VI)

wherein n is from 1 to 8 and $R^{10}$, $R^{11}$, $R^{12}$ independently of one another, represent hydrogen or linear, branched, cyclic or heterocyclic organic radicals which are unsubstituted or optionally also substituted by heteroatoms.

14. The process according to claim 1, wherein the photoinitiator system comprises an anionic, cationic or neutral dye and a coinitiator.

15. The process according to claim 1, wherein a layer of the photopolymer formulation in step ii) is bonded to a substrate.

16. The process according to claim 15, wherein the layer of the photopolymer formulation is bonded to a further substrate.

17. The process according to claim 15, wherein the layer of photopolymer formulation and the substrate is bonded to one another by lamination or adhesive bonding.

* * * * *